(12) United States Patent
Meagher et al.

(10) Patent No.: US 11,473,141 B2
(45) Date of Patent: Oct. 18, 2022

(54) ENDPOINT DETECTION OF AMPLIFIED NUCLEIC ACIDS

(71) Applicant: National Technology & Engineering Solutions of Sandia, LLC, Albuquerque, NM (US)

(72) Inventors: Robert Meagher, Mountain House, CA (US); Chung-Yan Koh, Arlington, VA (US); Yooli Kim Light, Pleasanton, CA (US); Cameron Scott Ball, Los Altos, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 16/903,075

(22) Filed: Jun. 16, 2020

(65) Prior Publication Data
US 2020/0370116 A1 Nov. 26, 2020

Related U.S. Application Data

(62) Division of application No. 15/008,285, filed on Jan. 27, 2016, now Pat. No. 10,724,091.

(60) Provisional application No. 62/249,139, filed on Oct. 30, 2015, provisional application No. 62/114,510, filed on Feb. 10, 2015.

(51) Int. Cl.
*C12Q 1/6876* (2018.01)
*C12Q 1/6818* (2018.01)

(52) U.S. Cl.
CPC ......... *C12Q 1/6876* (2013.01); *C12Q 1/6818* (2013.01); *C12Q 2600/16* (2013.01)

(58) Field of Classification Search
CPC ............ C12Q 2565/101; C12Q 1/6853; C12Q 1/6818; C12Q 1/6876; C12Q 2527/107; C12Q 2563/107; C12Q 2600/16
See application file for complete search history.

(56) References Cited

U.S. PATENT DOCUMENTS

| | | | |
|---|---|---|---|
| 6,194,158 B1 | 2/2001 | Kroes et al. | |
| 6,410,278 B1 | 6/2002 | Notomi et al. | |
| 7,267,943 B1 * | 9/2007 | O'Connell | C12Q 1/701 435/5 |
| 8,585,916 B2 | 11/2013 | Perroud et al. | |
| 8,900,807 B2 | 12/2014 | Owen et al. | |
| 8,962,346 B2 | 2/2015 | Schaff et al. | |
| 9,074,243 B2 | 7/2015 | Tanner et al. | |
| 9,074,249 B2 | 7/2015 | Tanner et al. | |
| 9,304,128 B1 | 4/2016 | Koh et al. | |
| 9,304,129 B2 | 4/2016 | Schaff et al. | |
| 9,702,871 B1 | 7/2017 | Koh et al. | |
| 9,795,961 B1 | 10/2017 | Koh et al. | |
| 9,803,238 B1 | 10/2017 | Koh et al. | |
| 9,809,845 B2 * | 11/2017 | Narayanan | C12Q 1/6806 |
| 9,903,001 B1 | 2/2018 | Koh et al. | |
| 10,254,298 B1 | 4/2019 | Koh | |
| 2005/0277134 A1 | 12/2005 | Okano et al. | |
| 2008/0038734 A1 * | 2/2008 | Sorge | C12Q 1/6823 435/6.1 |
| 2012/0164645 A1 * | 6/2012 | Fu | C12Q 1/6818 435/6.11 |
| 2013/0171643 A1 | 7/2013 | Kubota et al. | |
| 2014/0031248 A1 | 1/2014 | Tanner et al. | |
| 2014/0099241 A1 | 4/2014 | Perroud et al. | |
| 2014/0211204 A1 * | 7/2014 | Stedtfeld | C12Q 1/686 356/244 |
| 2014/0349295 A1 * | 11/2014 | Hosaka | C12Q 1/6816 435/6.11 |

OTHER PUBLICATIONS

Thekisoe et al., "Stability of Loop-Mediated Isothermal Amplification (LAMP) Reagents and its Amplification Efficiency on Crude Trypanosome DNA Templates," J. Vet. Med. Sci, vol. 71, No. 4, pp. 471-475. (Year: 2009).*
Kouguchi et al., "Homogenous, real-time duplex loop-mediated isothermal amplification using a single fluorophore-labeled primer and an itercalator dye," Molecular and Cellular Probes, vol. 24, pp. 190-195 (Year: 2010).*
U.S. Appl. No. 13/423,008, filed Mar. 16, 2012, Koh et al.
U.S. Appl. No. 13/423,050, filed Mar. 16, 2012, Schaff et al.
U.S. Appl. No. 13/941,186, filed Jul. 12, 2013, Koh et al.
U.S. Appl. No. 14/090,040, filed Nov. 26, 2013, Koh et al.
U.S. Appl. No. 14/157,278, filed Jan. 16, 2014, Koh et al.
U.S. Appl. No. 14/546,876, filed Nov. 18, 2014, Koh et al.
U.S. Appl. No. 14/597,601, filed Jan. 15, 2015, Schaff et al.
U.S. Appl. No. 14/957,405, filed Dec. 2, 2015, Koh.
Altschul et al., "Basic Local Alignment Search Tool," *J. Mol. Biol.* 1990, 215:403-10.
Ball et al., "Quenching of unincorporated amplification signal reporters in reverse-transcription loop-mediated isothermal amplification enabling bright, single-step, closed-tube, and multiplexed detection of RNA viruses," *Anal. Chem.* 2016;88:3562-8.
Ball et al., Supporting Information for: "Quenching of unincorporated amplification signal reporters in reverse-transcription loop-mediated isothermal amplification enabling bright, single-step, closed-tube, and multiplexed detection of RNA viruses," *Anal. Chem.* 2016;88:3562-8 (7 pp.).
Berge et al., "Pharmaceutical salts," *J. Pharm. Sci.* 1977, 66(1):1-19.
Curtis et al., "Isothermal amplification using a chemical heating device for point-of-care detection of HIV-1," *PLoS One* 2012, 7(2): e31432 (6pp.).

(Continued)

Primary Examiner — Young J Kim
(74) Attorney, Agent, or Firm — Eschweiler & Potashnik, LLC; Madelynne J. Farber; Samantha Updegraff

(57) ABSTRACT

The present invention relates to probes and primers beneficial for conducting amplification assays, such as those including loop-mediated isothermal amplification reactions. Also described herein are methods for detecting targets using such probes and/or primers.

20 Claims, 15 Drawing Sheets

Specification includes a Sequence Listing.

(56) References Cited

OTHER PUBLICATIONS

Curtis et al., "Rapid detection of HIV-1 by reverse-transcription, loop-mediated isothermal amplification (RT-LAMP)," *J. Virol. Methods* 2008, 151(2):264-70.

Curtis et al., "Sequence-specific detection method for reverse transcription, loop-mediated isothermal amplification of HIV-1," *J. Virol. Methods* 2009, 81:966-72.

Dauner et al., "Development of a pan-serotype reverse transcription loop-mediated isothermal amplification assay for the detection of dengue virus," *Diagn. Microbiol. Infect. Dis.* 2015;83(1):30-36.

Francois et al., "Robustness of a loop-mediated isothermal amplification reaction for diagnostic applications," *FEMS Immunol. Med. Microbiol.* 2011, 62:41-8.

Goto et al., "Colorimetric detection of loop-mediated isothermal amplification reaction by using hydroxy naphthol blue," *Biotechniques* 2009, 46(3):167-72.

Hayes et al., "Epidemiology and transmission dynamics of West Nile virus disease," *Emerg. Infect. Dis.* 2005, 11(8):1167-73.

Iseki et al., "Development of a multiplex loop-mediated isothermal amplification (mLAMP) method for the simultaneous detection of bovine *Babesia* parasites," *J. Microbiol. Methods* 2007, 71(3):281-7.

Iwamoto et al., "Loop-mediated isothermal amplification for direct detection of *Mycobacterium tuberculosis* complex, *M. avium*, and *M. intracellulare* in sputum samples," *J. Clin. Microbiol.* 2003, 41(6):2616-22.

Kendrick et al., "Notes from the feld: Transmission of Chikungunya virus in the continental United States—Florida, 2014," *MMWR Morb Mortal Wkly Rep.* 2014, 63(48):1137.

Kouguchi et al., "Homogenous, real-time duplex loop-mediated isothermal amplification using a single fluorophore-labeled primer and an intercalator dye: Its application to the simultaneous detection of Shiga toxin genes 1 and 2 in Shiga toxigenic *Escherichia coli* isolates," *Mol. Cell. Probes* 2010, 24(4):190-5.

Kubota et al., "FRET-based assimilating probe for sequence-specific real-time monitoring of loop-mediated isothermal amplification (LAMP)," *Biol. Eng. Trans.* 2011, 4(2):81-100.

Mori et al., "Detection of loop-mediated isothermal amplification reaction by turbidity derived from magnesium pyrophosphate formation," *Biochem. Biophys. Res. Commun.* 2001, 289(1):150-4.

Mori et al., "Loop-mediated isothermal amplification (LAMP): a rapid, accurate, and cost-effective diagnostic method for infectious diseases," *J. Infect. Chemother.* 2009, 15:62-9.

Mori et al., "Loop-mediated isothermal amplification (LAMP): recent progress in research and development," *J. Infect. Chemother.* 2013, 19:404-11.

Nagamine et al., "Accelerated reaction by loop-mediated isothermal amplification using loop primers," *Mol. Cell. Probes* 2002, 16:223-9.

Naze et al., "Simultaneous detection and quantitation of Chikungunya, Dengue and West Nile viruses by multiplex RT-PCR assays and Dengue virus typing using high resolution melting," *J. Virol. Methods* 2009, 162(1-2):1-7.

Ninove et al., "RNA and DNA bacteriophages as molecular diagnosis controls in clinical virology: a comprehensive study of more than 45,000 routine PCR tests," *PLoS One* 2011, 6(2):e16142 (7 pp.).

Njiru et al., "Loop-mediated isothermal amplification (LAMP) method for rapid detection of *Trypanosoma brucei rhodesiense*," *PLoS Negl. Trop. Dis.* 2008, 2(2):e147 (8 pp.).

Notomi et al., "Loop-mediated isothermal amplification of DNA," *Nucl. Acids Res.* 2000, 28(12):e63 (7 pp.).

Parida et al., "Rapid and real-time detection of Chikungunya virus by reverse transcription loop-mediated isothermal amplification assay," *J. Clin. Microbiol.* 2007, 45(2):351-7.

Parida et al., "Real-time reverse transcription loop-mediated isothermal amplification for rapid detection of West Nile virus," *J. Clin. Microbiol.* 2004, 42(1):257-63.

Queyriaux et al., "Clinical burden of chikungunya virus infection," *Lancet Infect. Dis.* 2008, 8(1):2-3.

Rudolph et al., "Detection of acute HIV-1 infection by RT-LAMP," *PLoS One* 2015, 10(5):e0126609 (13 pp.).

Smith et al., "Comparison of biosequences," *Adv. Appl. Math.* 1981, 2(4):482-9.

Smith et al., "Identification of common molecular subsequences," *J. Mol. Biol.* 1981, 147(1):195-7.

Sun et al., "Mechanistic evaluation of the pros and cons of digital RT-LAMP for HIV-1 viral load quantification on a microfluidic device and improved efficiency via a two-step digital protocol," *Anal. Chem.* 2013, 85(3):1540-6.

Tanner et al., "Simultaneous multiple target detection in real-time loop-mediated isothermal amplification," *BioTechniques* 2012, 53(2):81-9.

Tanner et al., "Visual detection of isothermal nucleic acid amplification using pH-sensitive dyes," *Biotechniques* 2015, 58(2):59-68.

Tanner et al., Supplemental Material for: "Simultaneous multiple target detection in real-time loop-mediated isothermal amplification," *BioTechniques* 2012;53(2):81-9 (2 pp.).

Tanner et al., "Loop-Mediated Isothermal Amplification for Detection of Nucleic Acids," Current Protocols in Molecular Biology 2014; Unit 15.4, pp. 1-14.

Thiboutot et al., "Chikungunya: a potentially emerging epidemic?," *PLoS Negl. Trop. Dis.* 2010, 4(4):e623 (8 pp.).

Tomita et al., "Loop-mediated isothermal amplification (LAMP) of gene sequences and simple visual detection of products," *Nat. Protoc.* 2008, 3(5):877-82.

Yi et al., "Molecular zipper: a fluorescent probe for real-time isothermal DNA amplification," *Nucl. Acids Res.* 2006, 34(11):e81 (5 pp.).

Zhang et al., "PowerBLAST: A new network BLAST application for interactive or automated sequence analysis and annotation," *Genome Res.* 1997, 7(6):649-56.

\* cited by examiner

```
       F1c                    F2
5'-ATCGTATCGTCTCGCCATCTACCACCAGAGCTATATTCATATC-3' (MS2 FIP,SEQ ID NO:1)
   ||||||||||||
3'-TAGCATAGCAGA-5'                              (MS2 FIPc-12, SEQ ID NO:2)

F1c                    F2
5'-ATCGTATCGTCTCGCCATCTACCACCAGAGCTATATTCATATC-3' (MS2 FIP,SEQ ID NO:1)
   |||||||||||||
3'-TAGCATAGCAGAG-5'                             (MS2 FIPc-13, SEQ ID NO:3)
```

FIG. 2B

```
       F1c                         L1   F2
5'-TTGGCCGCCTCCATATTCATCATTTTCAGCTGCGTGACTATCATGT-3' (WNV FIP, SEQ ID NO:4)
   |||||||||||||||||||||||||
3'-AACCGGCGGAGGTATAAGTAGTAAA-5'                      (WNV FIPc-25, SEQ ID NO:5)

F1c                         L1   F2
5'-TTGGCCGCCTCCATATTCATCATTTTCAGCTGCGTGACTATCATGT-3' (WNV FIP, SEQ ID NO:4)
   ||||| |||||||||||||||||||
3'-AACCGACGGAGGTATAAGTAGTAAA-5'                      (WNV FIPc-25m, SEQ ID NO:6)

F1c                         L1   F2
5'-TTGGCCGCCTCCATATTCATCATTTTCAGCTGCGTGACTATCATGT-3' (WNV FIP, SEQ ID NO:4)
   ||||||||||
3'-AACCGGCGGA-5'                                     (WNV FIPc-10, SEQ ID NO:7)

F1c                         L1   F2
5'-TTGGCCGCCTCCATATTCATCATTTTCAGCTGCGTGACTATCATGT-3' (WNV FIP, SEQ ID NO:4)
   ||||| ||||
3'-AACCGCCGGA-5'                                     (WNV FIPc-10m, SEQ ID NO:8)
```

FIG. 2C

LoopF:   5'- Cy3-GATTCCGTAGTGTGAGCG-3'   0.8 µM
Quench:  3'-IBFQ-CTAAGGCATCACA-5'        0-2 µM
Tm ~ 50 °C @ 8 mM Mg$^{++}$

ENDPOINT DETECTION OF AMPLIFIED NUCLEIC ACIDS

CROSS-REFERENCE TO RELATED APPLICATION

This application is a divisional application of, and discloses subject matter that is related to subject matters disclosed in, co-pending parent application U.S. Ser. No. 15/008,285, filed Jan. 27, 2016 and entitled "ENDPOINT DETECTION OF AMPLIFIED NUCLEIC ACIDS" which claimed the benefit of U.S. Provisional Application No. 62/249,139, filed Oct. 30, 2015, as well as U.S. Provisional Application No. 62/114,510, filed Feb. 10, 2015, each of which is incorporated herein by reference in its entirety for any purpose. The present application claims the priority of its parent application, which is incorporated herein by reference in its entirety for any purpose.

STATEMENT OF GOVERNMENT INTEREST

This invention was made with Government support under contract no. DE AC04-94AL85000 awarded by the U.S. Department of Energy to Sandia Corporation and under contract no. R01AI098853 awarded by the National Institute of Allergy and Infectious Diseases (NIAID). The Government has certain rights in the invention.

REFERENCE TO A SEQUENCE LISTING APPENDIX

A sequence listing appendix including an ASCII formatted file accompanies this application. The appendix includes a file named "SD13252_3_DIV_ST25.txt," created on Jun. 10, 2020 (size of 8.99 kilobytes), which is hereby incorporated by reference in its entirety.

FIELD OF THE INVENTION

The present invention relates to probes and primers beneficial for conducting amplification assays, such as those including loop-mediated isothermal amplification reactions. Also described herein are methods for detecting targets using such probes and/or primers.

BACKGROUND OF THE INVENTION

Nucleic acid amplification reactions provide a useful technique to detect low levels of targets, such as those from pathogenic viruses or bacteria. In general, such amplification reactions require cumbersome manipulation of reagents or elaborate instrumentation. In particular, for a loop-mediated isothermal amplification (LAMP) reaction, multiplexed detection of different targets can be difficult to achieve, especially in resource-limited conditions. Accordingly, there is a need for additional probes, primers, and methods to achieve sensitive detection of target nucleic acid in various experimental conditions.

SUMMARY OF THE INVENTION

The present invention relates to improved probe and primer sets that can be employed in nucleic acid amplification reactions. In particular, the probes are designed to minimize inhibition during the amplification phase of the reaction, as well as to maximize signal generation once the amplification phase has completed. In one particular embodiment, the probe is designed to have a characteristic melting temperature $T_m$ (e.g., determined under stringent conditions or any other condition described herein) that is lower that the temperature at which the amplification reaction is conducted (e.g., at temperature $T_2$). Desired $T_m$ values can be configured by designing the nucleic acid sequence of the probe (e.g., the quench probe and/or the signal probe) to have a short length (e.g., of from about 7 to 15 nucleotides) and/or one or more mismatches (e.g., one or more internal and/or terminal mismatches, as compared to sequence having perfect complementarity to the primer sequence or a portion thereof). One or more probes and primers herein can be provided in any useful format (e.g., as an assay or a package having individually stored reagents).

Furthermore, the present invention includes a method for detecting a presence of a target nucleic acid in a sample (e.g., by employing one or more primers, probes, or assays described herein). In particular, the method includes conducting the amplification reaction (e.g., by combining the sample with one or more reagents to amplify the target nucleic acid, if present) and then promoting hybridization of a quench probe to a primer by cooling (e.g., to a temperature $T_3$, where $T_3$ is less than the temperature $T_1$ at which amplification is conducted). In some embodiments, the method thereby provides a discriminated endpoint signal indicative of a presence or an absence of the target nucleic acid. In some embodiments, $T_3$ is a temperature of from about 55° C. or lower (e.g., of from about 10° C. to about 55° C.).

As described herein, each of the primers, probes, assays, and methods herein can be implemented in a multiplexed manner. Additional details follow.

Definitions

As used herein, the term "about" means +/−10% of any recited value. As used herein, this term modifies any recited value, range of values, or endpoints of one or more ranges.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, cDNA, DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs.

The term "modified," as used in reference to nucleic acids, means a nucleic acid sequence including one or more modifications to the nucleobase, nucleoside, nucleotide, phosphate group, sugar group, and/or internucleoside linkage (e.g., phosphodiester backbone, linking phosphate, or a phosphodiester linkage).

The nucleoside modification may include, but is not limited to, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyl-adenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, and combinations thereof.

A sugar modification may include, but is not limited to, a locked nucleic acid (LNA, in which the 2'-hydroxyl is connected by a $C_{1-6}$ alkylene or $C_{1-6}$ heteroalkylene bridge to the 4'-carbon of the same ribose sugar), replacement of the oxygen in ribose (e.g., with S, Se, or alkylene, such as methylene or ethylene), addition of a double bond (e.g., to replace ribose with cyclopentenyl or cyclohexenyl), ring contraction of ribose (e.g., to form a 4-membered ring of cyclobutane or oxetane), ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone), multicyclic forms (e.g., tricyclic), and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with a-L-threo-furanosyl-(3'→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar.

A backbone modification may include, but is not limited to, 2'-deoxy- or 2'-O-methyl modifications. A phosphate group modification may include, but is not limited to, phosphorothioate, phosphoroselenates, boranophosphates, boranophosphate esters, hydrogen phosphonates, phosphoramidates, phosphorodiamidates, alkyl or aryl phosphonates, phosphotriesters, phosphorodithioates, bridged phosphoramidates, bridged phosphorothioates, or bridged methylene-phosphonates.

"Complementarity" or "complementary" refers to the ability of a nucleic acid to form hydrogen bond(s) with another nucleic acid sequence by either traditional Watson-Crick or other non-traditional types, e.g., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" or "sufficient complementarity" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N. Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. Hybridization and washing conditions are well known and exemplified in Sambrook J, Fritsch E F, and Maniatis T, "Molecular Cloning: A Laboratory Manual," Second Edition, Cold Spring Harbor Laboratory Press, Cold Spring Harbor (1989), particularly Chapter 11 and Table 11.1 therein; and Sambrook J and Russell W, "Molecular Cloning: A Laboratory Manual," Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides). Furthermore, the skilled artisan will recognize that the temperature and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., *J. Mol. Biol.* 1990; 215:403-10; Zhang J et al., *Genome Res.* 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., *Adv. Appl. Math.* 1981; 2(4):482-9).

The term "fragment" is meant a portion of a nucleic acid that is at least one nucleotide shorter than the reference sequence. This portion contains, preferably, at least about 10%, 20%, 30%, 40%, 50%, 60%, 70%, 80%, or 90% of the entire length of the reference nucleic acid molecule. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides. In one example, any nucleic acid fragment can include a stretch of at least about 5 (e.g., about 7, about 8, about 10, about 12, about 14, about 18, about 20, about 24, about 28, about 30, or more) nucleotides that are at least about 40% (about 50%, about 60%, about 70%, about 80%, about 90%, about 95%, about 87%, about 98%, about 99%, or about 100%) identical to any of the sequences described herein can be utilized in accordance with the invention.

As used herein, when a nucleic acid sequence is referred to as having "at least X % sequence identity" to a reference sequence, it is meant that at least X percent of the nucleotides in the nucleic acid are identical to those of the reference sequence when the sequences are optimally aligned. An optimal alignment of sequences can be determined in various ways that are within the skill in the art, for instance, the Smith Waterman alignment algorithm (Smith T F et al., *Mol. Biol.* 1981; 147:195-7) and BLAST (Basic Local Alignment Search Tool; Altschul S F et al., *Mol. Biol.* 1990; 215:403-10). These and other alignment algorithms are accessible using publicly available computer software such as "Best Fit" (Smith T F et al., *Adv. Appl. Math.* 1981; 2(4):482-9) as incorporated into GeneMatcher Plus™ (Schwarz and Dayhof, "Atlas of Protein Sequence and Structure," ed. Dayhoff, M. O., pp. 353-358, 1979), BLAST, BLAST-2, BLAST-P, BLAST-N, BLAST-X, WU-BLAST-2, ALIGN, ALIGN-2, CLUSTAL, T-COFFEE, MUSCLE, MAFFT, or Megalign (DNASTAR). In addition, those skilled in the art can determine appropriate parameters for measuring alignment, including any algorithms needed to achieve optimal alignment over the length of the sequences being compared. For example, a nucleic acid sequence can have at least about 50%, 60%, 70%, 75%, 80%, 85%, 90%, 95%, 96%, 97%, 98%, 99%, or 100% sequence identity to the reference nucleic acid sequence. In general, for nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, or more nucleotides, up to the entire length of the nucleic acid molecule. It is understood that for the purposes of determining sequence identity when comparing a DNA sequence to an RNA sequence, a thymine nucleotide is equivalent to a uracil nucleotide.

By "substantial identity" or "substantially identical" is meant a nucleic acid sequence that has the same nucleic acid sequence as a reference sequence or has a specified percentage of nucleotides that are the same at the corresponding location within a reference sequence when the two sequences are optimally aligned. For example, a nucleic acid sequence that is "substantially identical" to a reference sequence has at least about 50%, 60%, 70%, 75%, 80%, 85%, 90%, 95%, 96%, 97%, 98%, 99%, or 100% sequence identity to the reference nucleic acid sequence. For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis., 53705). Such software may match similar sequences by assigning degrees of homology to various substitutions, deletions, and other modifications.

A "target sequence" as used herein is a polynucleotide (e.g., as defined herein, including a DNA, RNA, or DNA/RNA hybrid, as well as modified forms thereof) that includes a "target site." The terms "target site" is used to refer to a nucleic acid sequence present in a target genomic sequence (e.g., DNA or RNA in a host or pathogen) to which a primer (e.g., any herein) will bind provided sufficient conditions (e.g., sufficient complementarity) for binding exist. Suitable DNA/RNA binding conditions include physiological conditions normally present in a cell. Other suitable DNA/RNA binding conditions (e.g., conditions in a cell-free system) are known in the art; see, e.g., Sambrook, supra.

By "linker" is meant any useful multivalent (e.g., bivalent) component useful for joining to different portions or segments. Exemplary linkers include a nucleic acid sequence, a chemical linker, etc. For example, the linker can have a length of from about 3 nucleotides (nt) to about 90 nt, from about 3 nucleotides (nt) to about 80 nt, from about 3 nucleotides (nt) to about 70 nt, from about 3 nucleotides (nt) to about 60 nt, from about 3 nucleotides (nt) to about 50 nt, from about 3 nucleotides (nt) to about 40 nt, from about 3 nucleotides (nt) to about 30 nt, from about 3 nucleotides (nt) to about 20 nt or from about 3 nucleotides (nt) to about 10 nt. For example, the linker can have a length of from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. In some embodiments, the linker of a single-molecule guiding component is 4 nt. Other exemplary linkers include polyethylene glycol, an alkane chain, an alkylene group, a click-chemistry linker, a polynucleotide (e.g., poly(T), $(T)_n$, poly(G), $(G)_n$, $(GGGS)_n$, where n is any useful integer, such as 1, 2, 3, 4, 5, 6, 7, 8, 9, 10, etc.), and/or a carbocyclic ring (e.g., an aromatic ring, such as a phenyl group).

"Operably linked" or "operatively linked" or "operatively associated with," as used interchangeably, refers to a juxtaposition wherein the components so described are in a relationship permitting them to function in their intended manner. A first component can be operably linked to a second component by way of any useful bond (e.g., a covalent bond, a non-covalent bond, and/or linked via van der Waals forces, hydrogen bonds, and/or other intermolecular forces, such as those including a π-π interaction, a salt bridge, or a cation-π interaction) or any useful linker (e.g., any herein).

By "salt" is meant an ionic form of a compound or structure (e.g., any nucleic acid sequence, reagent, compounds, or compositions described herein), which includes a cation or anion compound to form an electrically neutral compound or structure. Salts are well known in the art. For example, non-toxic salts, pharmaceutically acceptable salts are described in Berge S M et al., "Pharmaceutical salts," *J. Pharm. Sci.* 1977 January; 66(1):1-19; and in "Handbook of Pharmaceutical Salts: Properties, Selection, and Use," Wiley-VCH, April 2011 (2nd rev. ed., eds. P. H. Stahl and C. G. Wermuth). The salts can be prepared in situ during the final isolation and purification of the compounds of the invention or separately by reacting the free base group with a suitable organic acid (thereby producing an anionic salt) or by reacting the acid group with a suitable metal or organic salt (thereby producing a cationic salt). Representative anionic salts include acetate, adipate, alginate, ascorbate, aspartate, benzenesulfonate, benzoate, bicarbonate, bisulfate, bitartrate, borate, bromide, butyrate, camphorate, camphorsulfonate, chloride, citrate, cyclopentanepropionate, digluconate, dihydrochloride, diphosphate, dodecyl sulfate, edetate, ethanesulfonate, fumarate, glucoheptonate, glucomate, glutamate, glycerophosphate, hemisulfate, heptonate, hexanoate, hydrobromide, hydrochloride, hydroiodide, hydroxyethanesulfonate, hydroxynaphthoate, iodide, lactate, lactobionate, laurate, lauryl sulfate, malate, maleate, malonate, mandelate, mesylate, methanesulfonate, methylbromide, methylnitrate, methylsulfate, mucate, 2-naphthalenesulfonate, nicotinate, nitrate, oleate, oxalate, palmitate, pamoate, pectinate, persulfate, 3-phenylpropionate, phosphate, picrate, pivalate, polygalacturonate, propionate, salicylate, stearate, subacetate, succinate, sulfate, tannate, tartrate, theophyllinate, thiocyanate, triethiodide, toluenesulfonate, undecanoate, valerate salts, and the like. Representative cationic salts include metal salts, such as alkali or alkaline earth salts, e.g., barium, calcium (e.g., calcium edetate), lithium, magnesium, potassium, sodium, and the like; other metal salts, such as aluminum, bismuth, iron, and zinc; as well as nontoxic ammonium, quaternary ammonium, and amine cations, including, but not limited to ammonium, tetramethylammonium, tetraethylammonium, methylamine, dimethylamine, trimethylamine, triethylamine, ethylamine, pyridinium, and the like. Other cationic salts include organic salts, such as chloroprocaine, choline, dibenzylethylenediamine, diethanolamine, ethylenediamine, methylglucamine, and procaine.

By "microfluidic" or "micro" is meant having at least one dimension that is less than 1 mm. For instance, a microfluidic structure (e.g., any structure described herein) can have a length, width, height, cross-sectional dimension, circumference, radius (e.g., external or internal radius), or diameter that is less than 1 mm.

The terms "Quenching of Unincorporated Primers" or "QUIP" and "Quenching of Unincorporated Amplification Signal Reporter" or "QUASR" are employed herein and can be used interchangeably.

Other features and advantages of the invention will be apparent from the following description and the claims.

BRIEF DESCRIPTION OF THE DRAWINGS

(FIG. 1C) the forward primers 121,122,123 and backward primers 125,126,127; and (FIG. 1D) the second and third amplicons 102,103.

FIG. 2A-2C provides exemplary quench probes hybridized to sufficiently complementary primer sequences. In particular, provided are (FIG. 2A) schematics of non-limiting quench probes and its sufficiently complementary primers; (FIG. 2B) exemplary nucleic acid sequences for a primer (MS2 FIP, SEQ ID NO: 1) and related quench probes (SEQ ID NOs: 2-3); and (FIG. 2C) further nucleic acid sequences for a primer (WNV FIP, SEQ ID NO:4) and related quench probes (SEQ ID Nos:5-8).

(FIG. 4B) a non-limiting binding configuration 403 for an FIP primer and probes; and (FIG. 4C) another non-limiting binding configuration 404 for an FIP primer and probes.

FIG. 8 shows detection of bacteriophage MS2 using a Cy3-labeled Loop primer (SEQ ID NO:36) and a complementary quencher (SEQ ID NO:37). Effective quenching of positive reactions was observed at all concentrations of quencher tested in excess of the Loop primer concentration. A bright signal was observed in the absence of the quencher, as expected. Use of the loop primers presents an alternative to the inner primers, in case secondary structure (e.g., hairpin formation) precludes design of a quenched probe that anneals well below the reaction temperature. The amplification reaction was conducted for 45 minutes at about 63° C. Reaction tubes were exposed to an excitation source with a green light emitting diode (LED) and a 500-540 nm bandpass (BP) filter and emission signals were imaged through a 550 nm low pass (LP) filter.

FIG. 9 provides fluorogenic detection of Ebola virus (EBOV) RNA by RT-LAMP using QUIP technique and three labeled loop primers for the GP, VP30, and L genes of the EBOV genome.

DETAILED DESCRIPTION OF THE INVENTION

The present invention relates to the use of a quench probe (e.g., any described herein) to improve endpoint detection after a nucleic amplification reaction (e.g., a LAMP reaction).

Figure 1A:
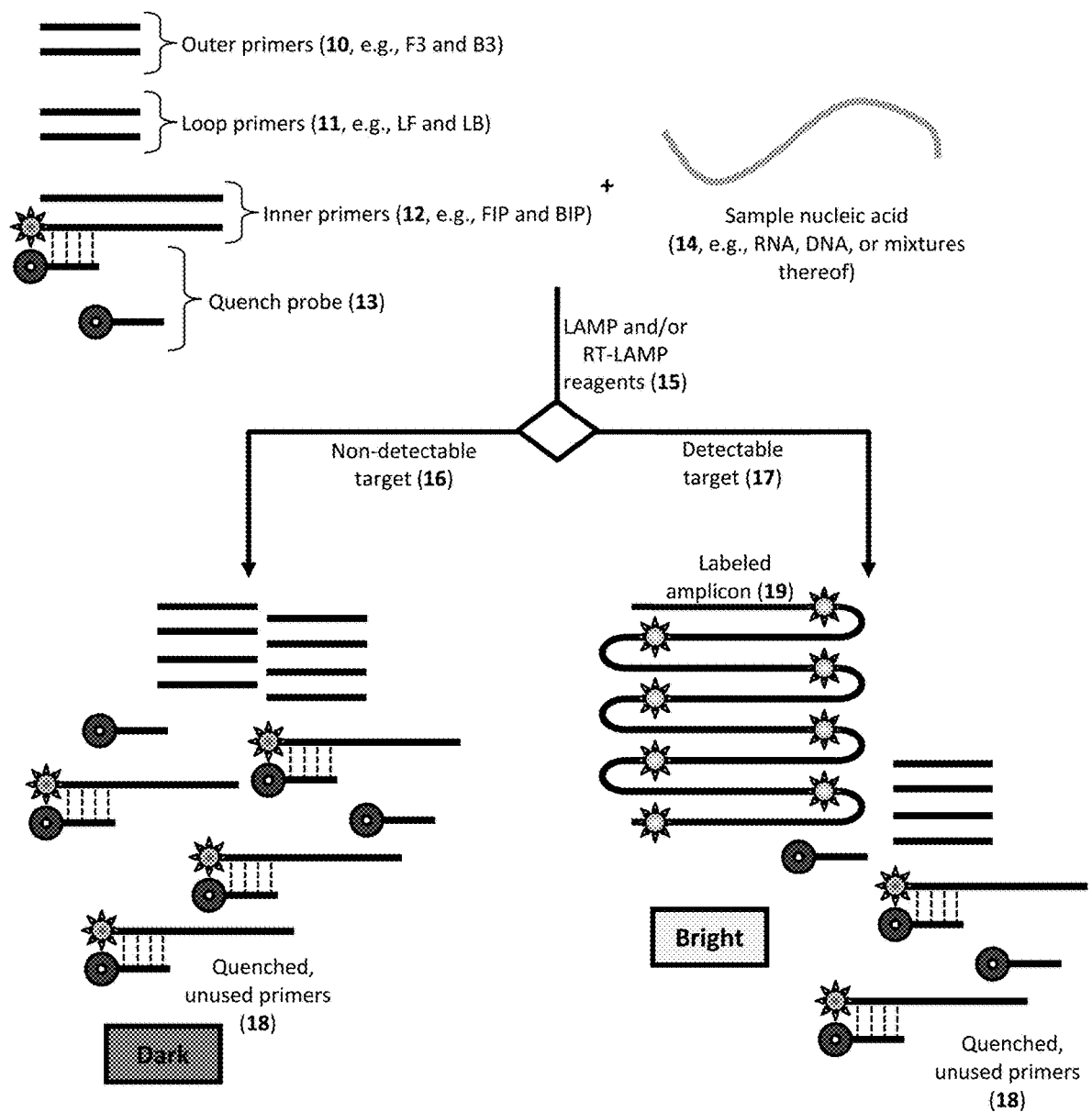
FIG. 1A-1D provides a non-limiting example of endpoint detection of loop-mediated isothermal amplification. Provided are (FIG. 1A) a schematic illustration of Quenching of UnIncorporated Primers (QUIP) for endpoint detection of loop-mediated isothermal amplification (LAMP), as well as (FIGS. 1B-1D) exemplary amplicons and associated primers for an exemplary LAMP reaction, including schematics of (FIG. 1B) the target nucleic acid 100 bound to the first amplicon 101.

FIG. 1A provides an exemplary method including the use of outer primers 10 (F3 or B3), the loop primers 11 (LoopF and LoopB), and/or the inner primers 12 (FIP or BIP) designed to bind to the desired target nucleic acid sequence. In this particular embodiment, one of the inner primers 12 includes a fluorescent label (e.g., a fluorophore at the 5'-terminus). The reaction mixture also includes a quench probe 13 having sufficient complementarity to a portion of an inner primer 12.

To begin the QUIP method, the primers (e.g., outer primers 10, loop primers 11, and inner primers 12, in which the loop primers are beneficial but only optional) and the probe (e.g., the quench probe 13, generally in excess of the concentration of at least one primer) are combined with a sample including a sample nucleic acid 14. In addition, one or more reagents 15, such as LAMP reagents (for a target DNA) or RT-LAMP reagents (for a target RNA), are included in the mixture, in which such reagents can include one or more enzymes (e.g., polymerases and/or reverse transcriptases), buffer, water, salts, nucleotides, divalent cations (e.g., $Mg^{++}$), or enhancing agents (e.g., betaine, dimethyl sulfoxide, ethylene glycol, glycerol, formamide, 7-deaza-2'-deoxyguanosine 5'-triphosphate, 2'-deoxyinosine 5'-triphosphate, or 1,2-propanediol). The mixture can be incubated for any useful time (e.g., about 20 to about 60 minutes) at any useful temperature (e.g., from about 60° C. to about 65° C.) to promote amplification.

As amplification proceeds and if the target is present 17, the fluorophore-labeled primers are incorporated into the amplicon 19 to provide a bright signal. If the target nucleic is not present or is undetectable 16, then the reaction mixture remains "dark" because unused labeled primers will have hybridized to quench probes to form a duplex 18 of quenched, unused primers.

In particular embodiments, to promote hybridization of the quench probes to any unused primer, the temperature of the reaction mixture is cooled, thereby increasing signal discrimination between positive and negative detection of the target.

Figure 1B:
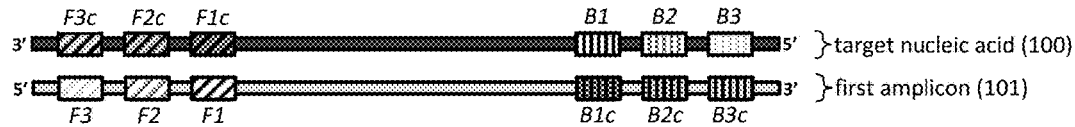
Figure 1C:
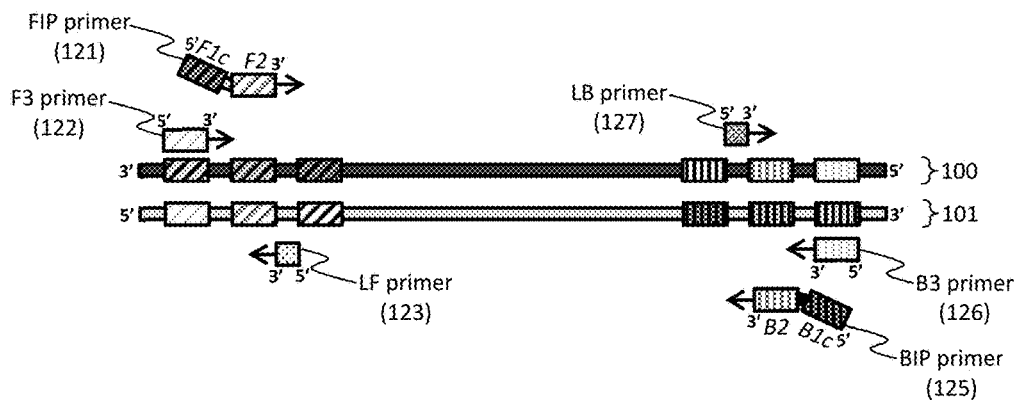
Figure 1D:
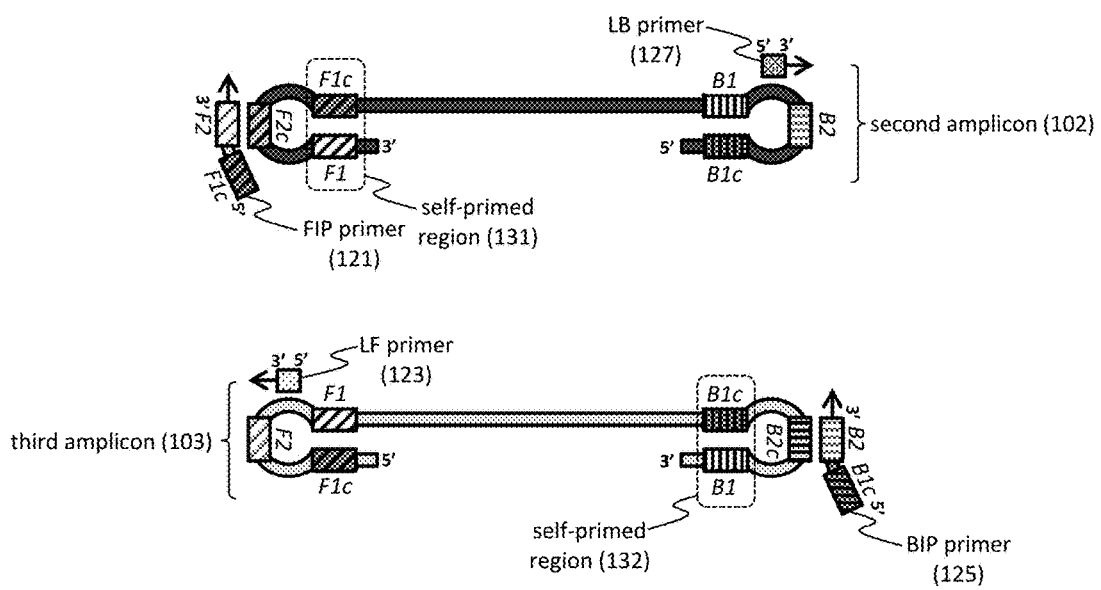

The primers can be designed in any useful manner. As seen in FIG. 1B-1D, the LAMP reaction (and RT-LAMP reaction) relies on a set of primers that bind to particular regions (labeled F1c, F2c, F3c, B1, B2, and B3) of the target nucleic acid 100. One exemplary amplicon 101 of the target nucleic acid 100 is shown, which is perfectly complementary to the target nucleic acid 100. The amplicon 101 has corresponding regions that are perfectly complementary to a region in the target nucleic acid (labeled F1, F2, F3, B1c, B2c, and B3c). Thus, as seen in FIG. 1B, the target nucleic acid 100 and amplicon 101 are positioned to have perfectly complementary regions facing each other.

As seen in FIG. 1C-1D, exemplary primers include the forward inner primer FIP 121 (having a F1c region linked to a F2 region), the forward primer F3 122 (having a F3 region), the loop forward primer LF 123 (having a complementary to the region between F1 and F2), the backward inner primer BIP 125 (having a B1c region linked to a B2 region), the backward primer B3 126 (having a B3 region), and the loop backward primer BF 127 (having a complementary to the region between B1 and B2). These primers can be designed to bind the first amplicon 101, as well as resulting amplicons 102, 103 having any useful sequence or structure (e.g., a dumbbell structure having self-primed regions 131, 132).

Figure 2A:
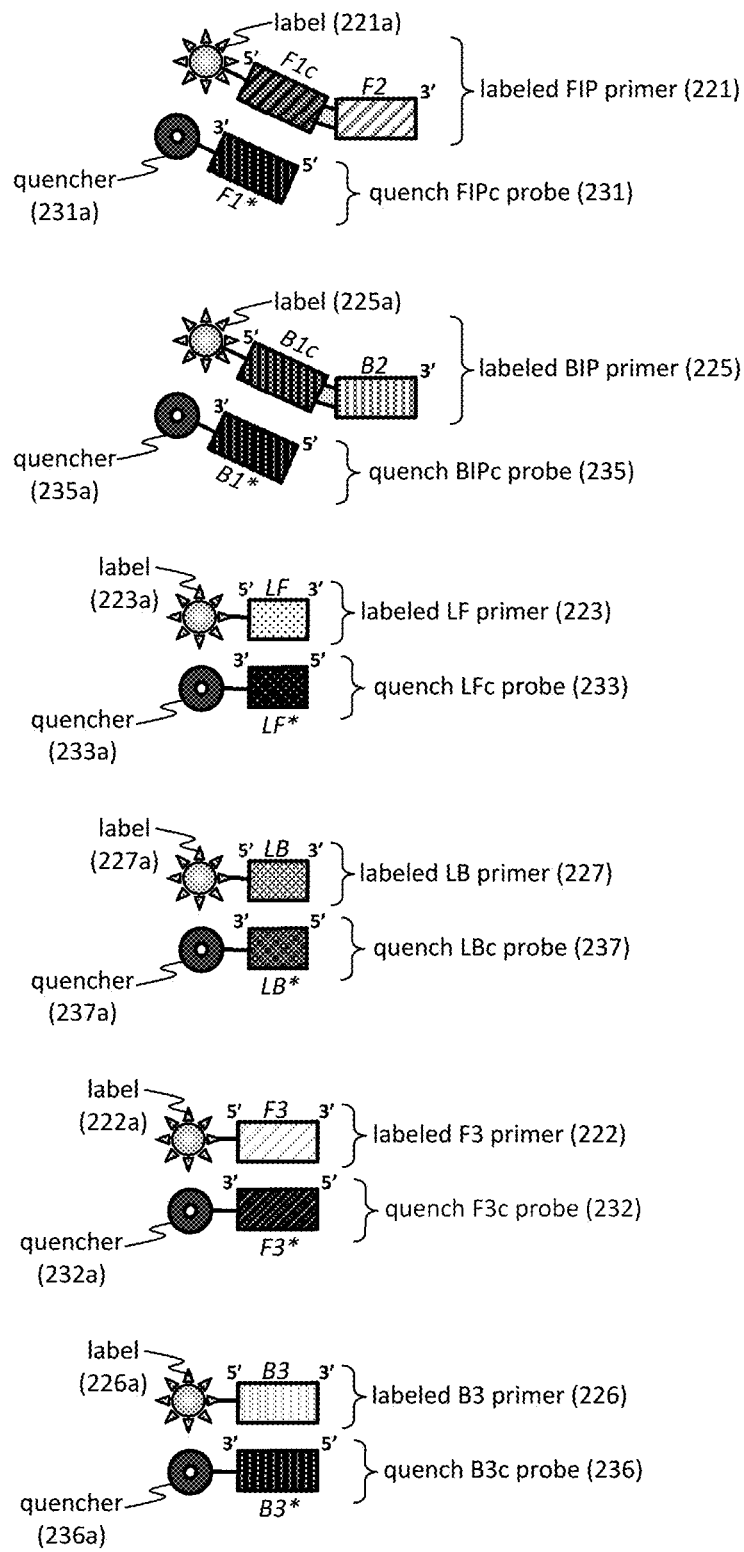

Furthermore, the primer and/or quench probe can include any useful label. In addition, the quench probe can include a nucleic acid sequence having sufficient complementarity to a portion of a primer. As seen in FIG. 2A, any primer can be labeled, and a corresponding quench probe can be designed to ensure that the quencher label of the probe is in sufficient proximity to the label of primer once the quench probe and the primer is hybridized. Exemplary primers include primers 221-223,225-227 having a fluorescent label 221a-223a, 225a-227a, which can hybridize to a quench probe 231-233, 235-237 having a quencher labels 231a-233a,235a-237a. Further exemplary primers and quench probes are described in FIG. 2B-2C, showing the position of fluorescent labels and quencher labels after hybridization.

Figure 3:
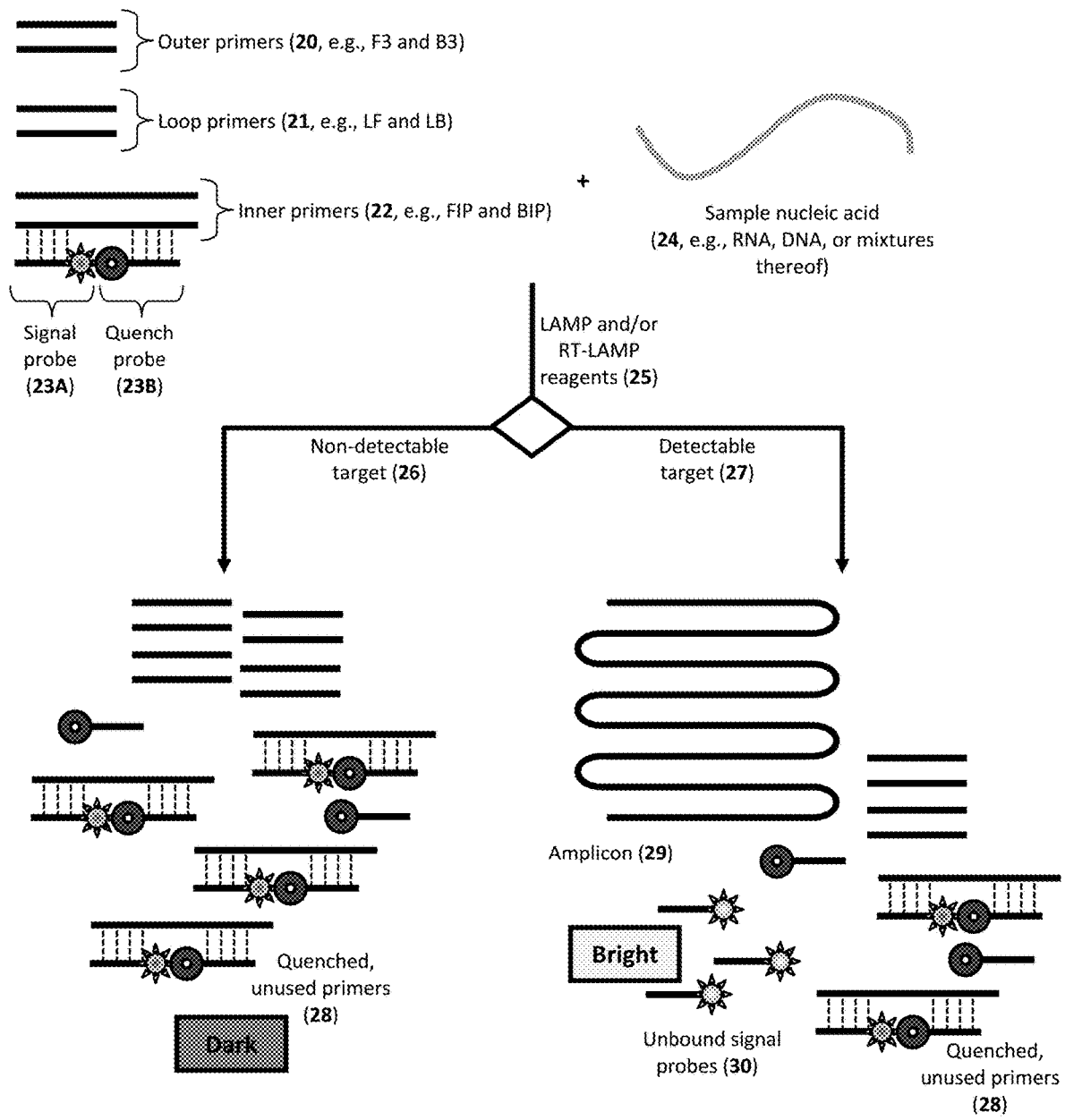
FIG. 3 provides another non-limiting example of endpoint detection of loop-mediated isothermal amplification using a quench probe and a signal probe.

FIG. 3 provides another exemplary method including the use of outer primers 20 (F3 or B3), the loop primers 21 (LoopF and LoopB), and/or the inner primers 22 (FIP or BIP) designed to bind to the desired target nucleic acid sequence. In this particular embodiment, the reaction mixture includes a quench probe 23B having sufficient complementarity to a first portion of an inner primer 22 and a signal probe 23A having sufficient complementarity to a second portion of an inner primer 22. The quench probe includes a quencher label, whereas the signal probe includes a fluorescent label. In this example, the primer need not be labeled.

The signal and quench probes can be designed to bind to any primer (e.g., inner, outer, or loop primer). Furthermore, the signal and quench probes are designed to ensure that the first and second portion of the primer are in proximity, such that the quencher label (of the quench probe) and the fluorescent label (of the signal probe) are in proximity to each other when the quench probe and the signal probe are hybridized to the first primer.

To begin thus QUIP method, the primers (e.g., outer primers 20, loop primers 21, and inner primers 22, in which the loop primers are beneficial but only optional) and the probe (e.g., the quench probe 23B, generally in excess of the concentration of at least one primer, and the signal probe 23A) are combined with a sample including a sample nucleic acid 24. In addition, one or more reagents 25, such as LAMP reagents (for a target DNA) or RT-LAMP reagents (for a target RNA), are included in the mixture.

As amplification proceeds and if the target is present 27, the amplicon 29 is not labeled, but the fluorophore-labeled signal probes 30 cannot hybridize to the primer, which is employed within the amplicon 29. Thus, the unbound signal probes 30 provide a bright signal, even if unused primers will have hybridized to quench probe and signal forms to form a duplex 28 of quenched, unused primers.

If the target nucleic is not present or is undetectable 26, then the reaction mixture remains "dark" because unused primers will have hybridized to quench probes and signal probes to form a duplex 28 of quenched, unused primers.

Figure 4A:
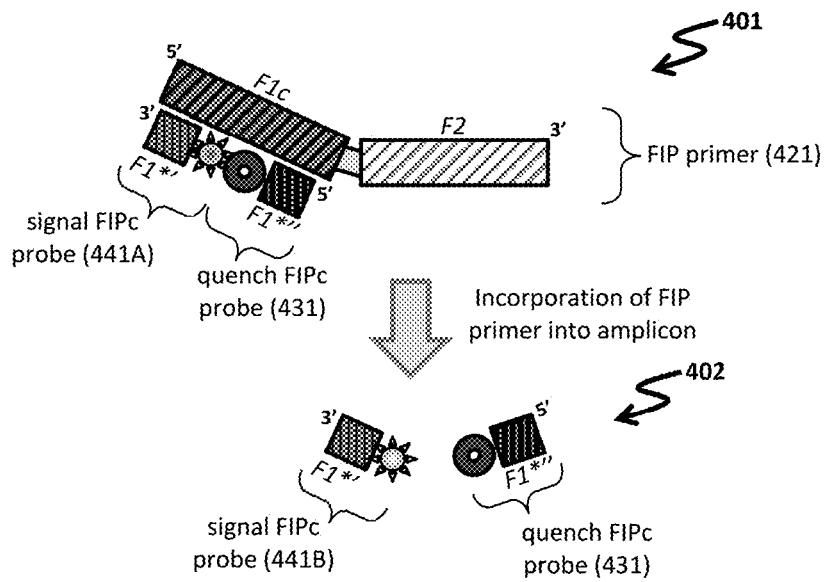
FIG. 4A-4C provides exemplary quench probes and signal probes hybridized to sufficiently complementary primer sequences. In particular, provided are schematics of (FIG. 4A) release of probes 441A-441B,431 after the FIP primer 421 is incorporated into an amplicon.

Furthermore, the quench probe and signal probe can be designed in any useful manner, so long as the label of each probe is in proximity when the probes are bound to the primer. As seen in FIG. 4A, the signal probe 441A can include a fluorescent label and a nucleic acid sequence having sufficient complementarity to a second portion of the FIP primer 421, and the quench probe 431 can include a quencher label and a nucleic acid sequence having sufficient complementarity to a first portion of the FIP primer 421. When hybridized to the FIP primer 421, the quencher label and the fluorescent label are in proximity to each other, thereby providing a dark mixture 401. Upon incorporation of the FIP primer into the amplicon, the primer is no longer available for hybridization, resulting in a bright mixture 402 having a released signal probe 441B.

Figure 4B:
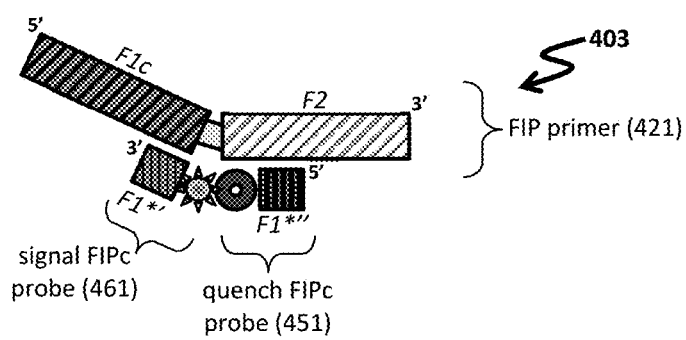
Figure 4C:
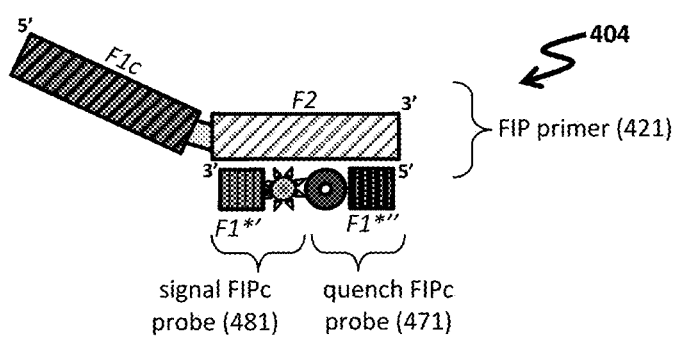

The signal and quencher probe can be designed to bind any portion of the primer. Different designs are provided in FIG. 4A-4C, including a quench probe 431,451,471 binding to a first portion that is in proximity to a second portion and a signal probe 441A,461,481 binding to the second portion. The labels are also arranged to ensure FRET (e.g., the fluorescent label on the 5'-terminus of the signal probe and the quencher label on the 3'-terminus of the quench probe; or the fluorescent label on the 3'-terminus of the signal probe and the quencher label on the 5'-terminus of the quench probe, depending on the position of the first and second portion, e.g., when the first portion is either downstream or upstream of the second portion).

Figure 5A:
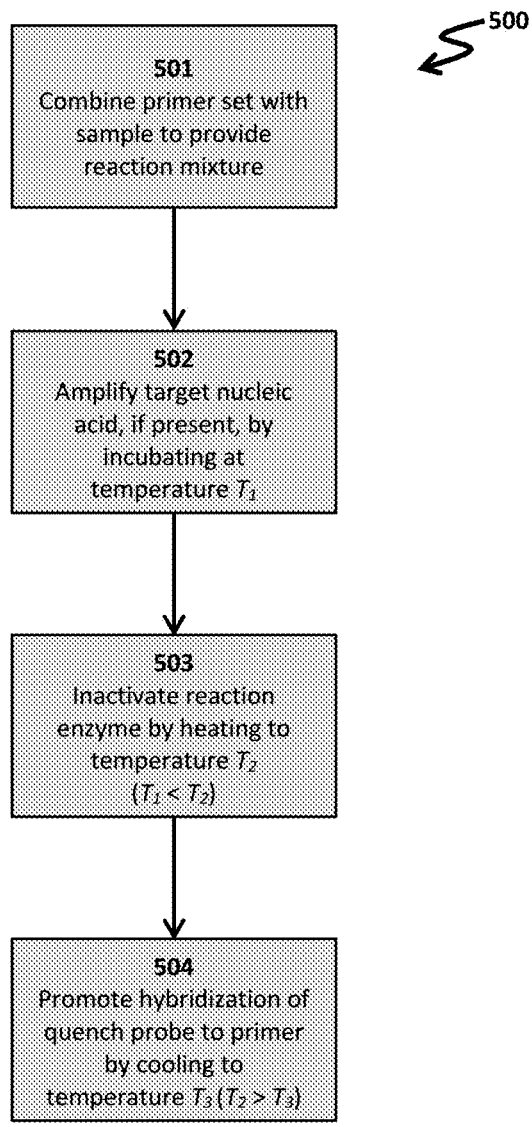
FIG. 5A-5B provides (FIG. 5A) a schematic of an exemplary method to detect a target nucleic acid sequence and (FIG. 5B) a schematic of an exemplary reaction scheme with temperatures $T_i$, $T_1$, $T_2$, and $T_3$.
Figure 5B:
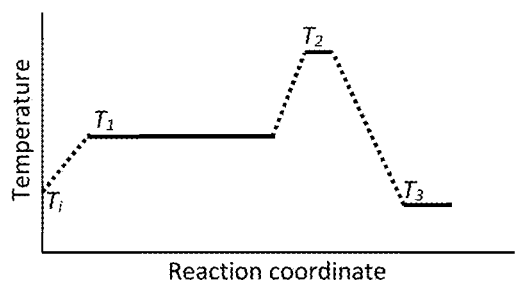

FIG. 5A-5B provides exemplary embodiments of methods. In one instance, as seen in FIG. 5A, the method includes combining 501 a sample with primer set (e.g., a first primer and a quench probe with an optional polymerase) to provide a reaction mixture, amplifying 502 the target nucleic acid sequence, if present, in the reaction mixture by incubating at a temperature $T_1$, and promoting 504 hybridization of the quench probe to the first primer by cooling to a temperature $T_3$ (e.g., where $T_3$ is less than $T_1$). In some embodiments, the method thereby provides a discriminated endpoint signal indicative of a presence or an absence of the target nucleic acid.

In further embodiments, the method further includes inactivating 503 the reaction enzyme by heating to a temperature $T_2$ (e.g., where $T_1$ is less than $T_2$). FIG. 5B provides one exemplary combination of temperatures, in which $T_1$ (initial temperature of the reagents) is less than $T_1$, $T_1$ is less than $T_2$, $T_2$ is greater than $T_3$, and/or, optionally, $T_3$ is less than both $T_2$ and $T_2$ (e.g., $T_2 < T_1 < T_3$).

The primer set can include any primer or probe described herein (e.g., where the primer is a first primer including a first nucleic acid sequence having sufficient complementarity to a site in the target nucleic acid, and where probe is a quench probe including a second nucleic acid sequence having sufficient complementarity to a first portion of the first primer and a quencher label operably linked to the second nucleic acid sequence).

Additional details on primer design, RT-LAMP conditions, and LAMP conditions, are described in U.S. Pat. Nos. 6,410,278, 8,900,807, 9,074,243, 9,074,249, U.S. Pub. No. 2013/0171643, as well as Notomi T et al., "Loop-mediated isothermal amplification of DNA," *Nucleic Acids Res.* 2000 Jun. 15; 28(12):e63 (7 pp.); and Parida M et al., "Real-time reverse transcription loop-mediated isothermal amplification for rapid detection of West Nile virus," *J. Clin. Microbiol.* 2004 January; 42(1):257-63), each of which is incorporated herein by reference in its entirety.

Primer and Probe Design

The primers of the invention can be designed to hybridize to the target nucleic acid sequence, or portions thereof, as well as amplicons derived from the target nucleic acid sequence. Furthermore, the primer (e.g., any herein, such as an inner primer, outer primer, or loop primer) can be labeled with a fluorescent label (e.g., for use with a quench probe) or can be unlabeled (e.g., for use with a quench probe and a signal probe). The concentration of the primer and probes can be optimized to promote the amplification reaction and/or to promote signal discrimination after the amplification reaction is conducted. In some instances, the concentration of the quench probe is greater than the concentration of the primer to which the quench probe is designed to hybridize.

As described herein, the quench probe can be designed to have a $T_m$ that is lower than the temperature at which the amplification reaction is generally conducted (e.g., a $T_1$ of from about 55° C. to about 65° C.). In some instance, the Tm of the quench probe is less than about 55° C. (e.g., of from about 10° C. to about 55° C., such as from 10° C. to 50° C., from 10° C. to 45° C., from 10° C. to 40° C., from 10° C. to 35° C., from 10° C. to 30° C., from 15° C. to 55° C., from 15° C. to 50° C., from 15° C. to 45° C., from 15° C. to 40° C., from 15° C. to 35° C., from 15° C. to 30° C., from 20° C. to 55° C., from 20° C. to 50° C., from 20° C. to 45° C., from 20° C. to 40° C., from 205° C. to 35° C., from 20° C. to 30° C., or from 20° C. to 25° C.). Such Tm can be designed by shortening the length of the nucleic acid sequence (e.g., to any length described herein) and/or introducing one or more base mismatches (e.g., internal and/or terminal mismatches).

Labels and Quenchers

The primers and probes herein can include any useful label, including fluorescent labels and quencher labels at any useful position in the nucleic acid sequence (e.g., at the 3'- and/or 5'-terminus).

Exemplary fluorescent labels include a quantum dot, a fluorophore), etc. Examples of fluorescence labels for use in this method includes fluorescein, 6-FAM™ (Applied Biosystems, Carlsbad, Calif.), TET™ (Applied Biosystems, Carlsbad, Calif.), VIC™ (Applied Biosystems, Carlsbad, Calif.), MAX, HEX™ (Applied Biosystems, Carlsbad, Calif.), TYE™ (ThermoFisher Scientific, Waltham, Mass.), TYE665, TYE705, TEX, JOE, Cy™ (Amersham Biosciences, Piscataway, N.J.) dyes (Cy2, Cy3, Cy3B, Cy3.5, Cy5, Cy5.5, Cy7), Texas Red® (Molecular Probes, Inc., Eugene, Oreg.), Texas Red-X, AlexaFluor® (Molecular Probes, Inc., Eugene, Oreg.) dyes (AlexaFluor 350, AlexaFluor 405, AlexaFluor 430, AlexaFluor 488, AlexaFluor 500, AlexaFluor 532, AlexaFluor 546, AlexaFluor 568, AlexaFluor 594, AlexaFluor 610, AlexaFluor 633, AlexaFluor 647, AlexaFluor 660, AlexaFluor 680, AlexaFluor 700, AlexaFluor 750), DyLight™ (ThermoFisher Scientific, Waltham, Mass.) dyes (DyLight 350, DyLight 405, DyLight 488, DyLight 549, DyLight 594, DyLight 633, DyLight 649, DyLight 755), ATTO™ (ATTO-TEC GmbH, Siegen, Germany) dyes (ATTO 390, ATTO 425, ATTO 465, ATTO 488, ATTO 495, ATTO 520, ATTO 532, ATTO 550, ATTO 565, ATTO Rho101, ATTO 590, ATTO 594, ATTO 610, ATTO 620, ATTO 633, ATTO 635, ATTO 637, ATTO 647, ATTO 647N, ATTO 655, ATTO 665, ATTO 680, ATTO 700, ATTO 725, ATTO 740), BODIPY® (Molecular Probes, Inc., Eugene, Oreg.) dyes (BODIPY FL, BODIPY R6G, BODIPY TMR, BOPDIPY 530/550, BODIPY 558/568, BODIPY 564/570, BODIPY 576/589, BODIPY 581/591, BODIPY 630/650, BODIPY 650/665), HiLyte Fluor™ (AnaSpec, Fremont, Calif.) dyes (HiLyte Fluor 488, HiLyte Fluor 555, HiLyte Fluor 594, HiLyte Fluor 647, HiLyte Fluor 680, HiLyte Fluor 750), AMCA, AMCA-S, Cascade® Blue (Molecular Probes, Inc., Eugene, Oreg.), Cascade Yellow, Coumarin, Hydroxycoumarin, Rhodamine Green™-X (Molecular Probes, Inc., Eugene, Oreg.), Rhodamine Red™-X (Molecular Probes, Inc., Eugene, Oreg.), Rhodamine 6G, TMR, TAMRA™ (Applied Biosystems, Carlsbad, Calif.), 5-TAMRA, ROX™ (Applied Biosystems, Carlsbad, Calif.), Oregon Green® (Life Technologies, Grand Island, N.Y.), Oregon Green 500, IRDye® 700 (Li-Cor Biosciences, Lincoln, Nebr.), IRDye 800, WellRED D2, WellRED D3, WellRED D4, and Lightcycler® 640 (Roche Diagnostics GmbH, Mannheim, Germany). In some embodiments, bright fluorophores with extinction coefficients >50,000 $M^{-1}$ $cm^{-1}$ and appropriate spectral matching with the fluorescence detection channels can be used.

In a specific embodiment, a fluorescently labeled primer is included in a reaction mixture and a fluorescently labeled reaction product is produced. Fluorophores used as labels to generate a fluorescently labeled primer included in embodiments of methods and compositions of the present invention can be any of numerous fluorophores including, but not limited to, those described in Haughland, R. P., The Handbook, A Guide to Fluorescent Probes and Labeling Technologies, 10th Ed., 2005; Lakowicz, J. R., Principles of Fluorescence Spectroscopy, Springer, 3rd ed., 2006; 4-acetamido-4'-isothiocyanatostilbene-2,2' disulfonic acid; acridine and derivatives such as acridine and acridine isothiocyanate; 4-amino-N-[3-vinylsulfonyl)phenyl] naphthalimide-3,5 disulfonate, Lucifer Yellow VS; N-(4-anilino-1-naphthyl)maleimide; anthranilamide, Brilliant Yellow; BIODIPY fluorophores (4,4-difluoro-4-bora-3a,4a-diaza-s-indacenes); coumarin and derivatives such as coumarin, 7-amino-4-methylcoumarin (AMC, Coumarin 120), 7-amino-4-trifluoromethylcoumarin (Coumaran 151); cyanosine; DAPDXYL sulfonyl chloride; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-4'-dimethylaminophenylazo)benzoic acid (DABCYL); 4-dimethylaminophenylazophenyl-4'-isothiocyanate (DABITC); EDANS (5-[(2-aminoethyl)amino]naphthalene-1-sulfonic acid), eosin and derivatives such as eosin isothiocyanate; erythrosin and derivatives such as erythrosin B and erythrosin isothiocyanate; ethidium such as ethidium bromide; fluorescein and derivatives such as 5-carboxyfluorescein (FAM), hexachlorofluorescenin, 5-(4,6-dichlorotriazin-2-yl)aminofluorescein (DTAF), 2',7'-dimethoxy-4',5'-dichloro-6-carboxyfluorescein (JOE) and fluorescein isothiocyanate (FITC); fluorescamine; green fluorescent protein and derivatives such as EBFP, EBFP2, ECFP, and YFP; IAEDANS (5-({2-[(iodoacetyl)amino]ethyl} amino) naphthalene-1-sulfonic acid), Malachite Green isothiocyanate; 4-methylumbelliferone; orthocresolphthalein; nitrotyrosine; pararosaniline; Phenol Red; B-phycoerytnin; o-phthaldialdehyde; pyrene and derivatives such as pyrene butyrate, 1-pyrenesulfonyl chloride and succinimidyl 1-pyrene butyrate; QSY 7; QSY 9; Reactive Red 4 (Cibacron® Brilliant Red 3B-A); rhodamine and derivatives such as 6-carboxy-X-rhodamine (ROX), 6-carboxyrhodamine (Rhodamine 6G), rhodamine isothiocyanate, lissamine rhodamine B sulfonyl chloride, rhodamine B, rhodamine 123, sulforhodamine B, sulforhodamine 101 and sulfonyl chloride derivative of sulforhodamine 101 (Texas Red); N,N,N', N-tetramethyl-carboxyrhodamine (TAMRA); tetramethyl rhodamine; tetramethyl rhodamine isothiocyanate (TRITC); riboflavin; rosolic acid and terbium chelate derivatives.

Exemplary quencher labels include a fluorophore, a quantum dot, a metal nanoparticle, etc.). Suitable quenchers include Black Hole Quencher®-1 (Biosearch Technologies, Novato, Calif.), BHQ-2, Dabcyl, Iowa Black® FQ (Integrated DNA Technologies, Coralville, Iowa), IowaBlack RQ, QXL™ (AnaSpec, Fremont, Calif.), QSY 7, QSY 9, QSY 21, QSY 35, and IRDye QC. In one instance, the term "quencher" refers to a substance which reduces emission from a fluorescent donor when in proximity to the donor. Fluorescence is quenched when the fluorescence emitted from the fluorophore is detectably reduced, such as reduced by 10%, 20%, 30%, 40%, 50%, 60%, 70%, 80%, 90%, 95%, 99% or more. Numerous fluorophore quenchers are known in the art, including, dabcyl; sulfonyl chlorides such as dansyl chloride; and Black Hole Quenchers BHQ-1, BHQ-2 and BHQ-3.

Any detection method or system operable to detect a labeled reaction product can be used in methods according to embodiments of the present invention and such appropriate detection methods and systems are well-known in the art. A signal from the fluorescently labeled reaction product is detected, for instance, using a UV light source, a LED light source, a flashlight, etc., such as from a mobile device or a smartphone.

Additional examples of fluorophore/quencher pairs are known in the art, for instance, described in Lakowicz, J. R., Principles of Fluorescence Spectroscopy, Springer, 3rd ed., 2006; and Haughland, R. P., The Handbook, A Guide to Fluorescent Probes and Labeling Technologies, 10th Ed., 2005, which is incorporated herein by reference in its entirety.

Multiplexing

The methods, probes, primers, and assays described herein are amenable to high-plex amplification. Multiplexing of samples and detection of amplification products can be achieved in a single reaction vessel as described herein. If desired, size determination can be performed by means of downstream analysis including capillary electrophoresis, which separates products based on size and can detect fluorescent labels.

Enzymes

Various embodiments of the assays and methods include use of one or more enzymes (e.g., a strand displacement polymerase or an archeal polymerase), including a plurality of polymerases. If the target nucleic acid includes a RNA sequence, or a portion of an RNA sequence, then a reverse transcriptase can be employed to reverse transcribe the RNA target into a DNA (e.g., cDNA) sequence.

Exemplary enzymes include Bst DNA polymerase, Bca (exo-)DNA polymerase, DNA polymerase I Klenow fragment, Vent DNA polymerase, Vent (exo-)DNA polymerase (Vent DNA polymerase deficient in exonuclease activity), Vent™ DNA polymerase, 9° N™ polymerase, Deep Vent DNA polymerase, Deep Vent (exo-)DNA polymerase (Deep Vent DNA polymerase deficient in exonuclease activity), Φ29 phage DNA polymerase, MS-2 phage DNA polymerase, Z-Taq DNA polymerase (Takara Shuzo Co., Ltd.), Taq polymerase, and KOD DNA polymerase (Toyobo Co., Ltd.), as well as variants thereof, such as Bst 2.0 or Bst 2.0 WarmStart™ DNA polymerases (New England Biolabs, Ipswich, Mass.) and combinations thereof (e.g., a blend of a strand displacement polymerase and Taq (see for example, OneTaq, New England Biolabs, Ipswich, Mass.)).

Kits

The present apparatus can further be provided in a kit. The kit can include one or more of the following: a primer, a probe (e.g., a quench probe and/or a signal probe), other reagents (e.g., any described herein, such as enzymes, buffer, or enhancing agents), and instructions for use (e.g., such as those including any method described herein). Each component of the kit can be packaged separately or together. In one instance, the components are packaged together to allow for a single chamber or single test tube reaction.

Methods of Use

The present probes, primers, assays, and methods can be used to detecting any target of interest (e.g., any described herein). In particular, the probes, primers, assays, and methods allow for single-step, closed tube reactions in a chamber that is disposable, thereby facilitating single-use detection of samples that could be easily contaminated or could be potentially hazardous (e.g., infectious). In some embodiments, the cartridge is configured for sensing a nucleic acid (e.g., DNA or RNA), as well as for detecting a pathogen (e.g., a bacterial pathogen, such as any herein), metabolite, genetic modification, and/or pesticide for any use (e.g., livestock monitoring, crop maintenance, as well as any other agricultural use).

Targets and Samples

The present cartridge can be used to detect any useful targets (e.g., a target nucleic acid or a nucleic acid sequence derived from the target or identifiable as the target). Exemplary targets include a bacterium, such as such as *Bacillus* (e.g., *B. anthracis*), Enterobacteriaceae (e.g., *Salmonella, Escherichia coli, Yersinia pestis, Klebsiella*, and *Shigella*), *Yersinia* (e.g., *Y. pestis* or *Y. enterocolitica*), *Staphylococcus* (e.g., *S. aureus*), *Streptococcus, Gonorrheae, Enterococcus* (e.g., *E. faecalis*), *Listeria* (e.g., *L. monocytogenes*), *Brucella* (e.g., *B. abortus, B. melitensis*, or *B. suis*), *Vibrio* (e.g., *V. cholerae*), *Corynebacterium diphtheria, Pseudomonas* (e.g., *P. pseudomallei* or *P. aeruginosa*), *Burkholderia* (e.g., *B. mallei* or *B. pseudomallei*), *Shigella* (e.g., *S. dysenteriae*), *Rickettsia* (e.g., *R. rickettsii, R. prow azekii*, or *R. typhi*), *Francisella tularensis, Chlamydia psittaci, Coxiella burnetii, Mycoplasma* (e.g., *M. mycoides*), etc.; an allergen, such as mycotoxins, mold spores, or bacterial spores such as *Clostridium botulinum* and *C. perfringens*; a toxin, such as ricin, mycotoxin, tetrodotoxin, anthrax toxin, botulinum toxin, *staphylococcal* entertoxin B, or saxitoxin; a virus, such as Adenoviridae (e.g., adenovirus), Arenaviridae (e.g., Machupo virus), Bunyaviridae (e.g., *Hantavirus* or Rift Valley fever virus), Coronaviridae, Orthomyxoviridae (e.g., influenza viruses), Filoviridae (e.g., Ebola virus and Marburg virus), Flaviviridae (e.g., Japanese encephalitis virus and Yellow fever virus), Hepadnaviridae (e.g., hepatitis B virus), Herpesviridae (e.g., herpes simplex viruses), Papovaviridae (e.g., papilloma viruses), Paramyxoviridae (e.g., respiratory syncytial virus, measles virus, mumps virus, or parainfluenza virus), Parvoviridae, Picornaviridae (e.g., polioviruses), Poxviridae (e.g., variola viruses), Reoviridae (e.g., rotaviruses), Retroviridae (e.g., human T cell lymphotropic viruses (HTLV) and human immunodeficiency viruses (HIV)), Rhabdoviridae (e.g., rabies virus), and Togaviridae (e.g., encephalitis viruses, yellow fever virus, and rubella virus)); a protozoon, such as *Cryptosporidium parvum, Encephalitozoa, Plasmodium, Toxoplasma gondii, Acanthamoeba, Entamoeba histolytica, Giardia lamblia, Trichomonas vaginalis, Leishmania*, or *Trypanosoma* (e.g., *T. brucei* and *T. Cruzi*); a helminth, such as cestodes (tapeworms), trematodes (flukes), or nematodes (roundworms, e.g., *Ascaris lumbricoides, Trichuris trichiura, Necator americanus*, or *Ancylostoma duodenale*); a parasite (e.g., any protozoa or helminths described herein); a fungus, such as *Aspergilli, Candidae, Coccidioides immitis*, and *Cryptococci*; a pathogen; an environmental contaminant; a water additive; an agricultural marker; a nucleic acid (e.g., oligonucleotides, polynucleotides, nucleotides, nucleosides, molecules of DNA, or molecules of RNA, including a chromosome, a plasmid, a viral genome, a primer, or a gene of any useful pathogen, such as those described herein); or a genetic modification (e.g., antibiotic resistance marker gene). Targets also include food-borne pathogens, such as *Salmonella* (e.g., *Salmonella Typhimurium*), pathogenic *E. coli* (e.g., O157:H7), *Bacillus* (e.g., *B. cereus*), *Clostridium botulinum, Listeria monocytogenes, Yersinia* (e.g., *Y. enterocolitica*), Norovirus (e.g., Norwalk virus), *Shigella, Staphylococcus aureus, Toxoplasma gondii, Vibrio* (e.g., *V. vulnificus, V. cholera, V. parahaemolyticus*), *Campylobacter jejuni*, and *Clostridium perfringens*; and weaponized pathogens, such as *Bacillus anthracis, Yersinia pestis, Francisella tularensis, Brucella* (e.g., *B. suis*), *Burkholderia mallei, Burkholderia pseudomallei, Shigella, Clostridium botulinum, Variola* (e.g., *V. major*), Filoviridae (e.g., Ebola virus and Marburg virus), Arenaviridae (e.g., Lassa virus and Machupo virus), *Clostridium perfringens*, any food-borne pathogen (e.g., *Salmonella* species, *Escherichia coli* O157: H7, or *Shigella*), *Chlamydia psittaci, Coxiella burnetii, Staphylococcal aureus, Rickettsia* (e.g., *R. prowazekii* or *R. rickettsii*), *Alphavirus* (e.g., Venezuelan equine encephalitis virus, eastern equine encephalitis virus, or western equine encephalitis virus), *Vibrio cholerae, Cryptosporidium parvum, Henipavirus* (e.g., Nipah virus), Bunyaviridae (e.g., *Hantavirus* or Rift Valley fever virus), Flaviviridae (e.g., Japanese encephalitis virus and Yellow fever virus), and *Coccidioides* spp.

The test sample can include any useful sample, such as a microorganism, a virus, a bacterium, a fungus, a parasite, a helminth, a protozoon, a cell, tissue, a fluid, a swab, a biological sample (e.g., blood, serum, plasma, saliva, etc.), a plant, an environmental sample (e.g., air, soil, and/or water), etc.

EXAMPLES

Example 1

Endpoint Detection of LAMP or RT-LAMP Reactions by Quenching of Unincorporated Labeled Primers Loop-mediated isothermal amplification (LAMP) is an isothermal nucleic acid amplification technique that is a useful alternative to polymerase chain reaction (PCR) for low-cost or point-of-care diagnostics for infectious disease. The technique can be coupled with reverse transcription (RT-LAMP) for detection of RNA targets, e.g., RNA viruses. LAMP (and RT-LAMP) is generally regarded as highly specific and highly sensitive, but a major challenge for point-of-care applications is the detection of amplification without requiring cumbersome manipulation or elaborate instrumentation. Furthermore, the available detection mechanisms are not easily amenable to multiplexing to detect multiple targets in a single reaction, e.g. for syndromic panels, whereas spectral multiplexing techniques exist for PCR that enable detection of a plurality of targets (e.g., 2, 3, 4, or more targets) per reaction.

The present invention can enable endpoint detection of nucleic acid amplification products from isothermal amplification reactions such as LAMP or RT-LAMP. The present invention is based on use of dye-labeled primers which are incorporated into amplification products if a target is present. Also present is a slight excess of a short quenching probe which does not participate in the amplification but hybridizes to the labeled primer upon cooling to ambient temperature at the end of the reaction. Labeled primer that remains unused hybridizes to the quenching probe, dramatically reducing fluorescence. Any primer that is incorporated into an amplification product is not quenched, resulting bright fluorescence that is retained at ambient temperature. The resulting fluorescence is discernible by naked eye, with >10-fold difference in brightness between positive and negative reactions. The present invention presents several advantages over other techniques reported for detecting amplification by LAMP.

In general, detection of amplification in LAMP (or RT-LAMP) usually takes the following two forms. In a first form, endpoint detection is employed. In this detection scheme, any useful technique can be employed, such as gel separation, in which the product is separated on a gel to observe a banding pattern; observation of turbidity; the addition of a large amount of intercalating dye (e.g., such as SYBR Green) to observe a color change and/or fluorescence signal; addition of manganese-quenched calcein, which results in a fluorescence signal upon amplification; and addition of a colorimetric indicator such as hydroxynaphthol blue (HNB), which results in a change in color from blue to violet upon amplification.

In a second form, real-time detection is employed. In this detection scheme, a change in an observable signal (e.g., turbidity or fluorescence) is measured as the reaction progressed. A fluorescent signal can arise from a non-inhibitory intercalating dye (e.g., such as SYTO® 9) or from manganese-quenched calcein.

Each of these endpoint and real-time detection techniques has specific advantages and disadvantages. For example, the turbidity measurement is subtle and difficult to see. Running the product on a gel or the addition of large amount of SYBR Green requires opening the reaction tube after amplification, which presents a major risk for amplicon contamination and requires extreme care, e.g., performing the endpoint analysis in a separate laboratory from where reactions are prepared. In addition, approaches using manganese-quenched calcein are reported to suffer from inhibition from manganese. The colorimetric technique with HNB is a subtle color change. Furthermore, the SYTO® family of dyes for real-time detection is non-inhibitory, but fluorescence detection must be performed at elevated temperature for maximum discrimination between positive and negative amplifications.

All of these detection techniques are non-sequence specific and detect total amplification. As such, they cannot be multiplexed to allow detection of more than one target. Several reports describe multiplexing by means of performing a post-reaction restriction digest and then running the product on a gel. Such a technique requires opening the tube (thereby increasing the risk for amplicon contamination), as well as several additional steps. A number of other reports describe multiplexing techniques specifically for real-time detection based on displacement of a bound quencher, or fluorescence resonance energy transfer (FRET), or combination of labeled primers and intercalating dyes.

In particular embodiments, real-time monitoring for LAMP or RT-LAMP is not required. In some instances, the reaction is semi-quantitative at best, with the time to positive detection being only weakly correlated to the amount of target present. As such, in some embodiments, endpoint monitoring is sufficient to distinguish positive from negative reactions. Particularly in the case of point-of-care detection, discriminating positive from negative at a defined endpoint (e.g., 30 minutes of amplification) is a reasonable and instrumentally simpler approach. In most situations, LAMP and RT-LAMP are not considered to be first-line test to obtain quantitative information on target concentration.

Herein, the present invention provides an optimized approach for endpoint determination of LAMP and RT-LAMP reactions, based upon Quenching of Unincorporated Primers (QUIP). Previously, we have found the most sensitive dyes for detection of LAMP amplification to be the SYTO® family of intercalating dyes (e.g., SYTO® 9, SYTO® 82, or SYTO® 62). Compared to the SYTO® dyes, the QUIP technique does not require detection at an elevated temperature (e.g., to increase the discrimination of the fluorescence signal, although, in some cases, elevated temperatures may be required to accelerate enzymatic action, e.g., polymerase and/or reverse transcriptase action). Furthermore, as compared to SYTO® dyes, QUIP provides a more intense signal, e.g., a larger difference in fluorescence intensity between positive and negative reactions, allowing easier discrimination. In some situations, the signal for QUIP can be strong enough to observe by naked eye with simple equipment (e.g., an LED flashlight, even one provided in a mobile device, with a colored plastic gel filter).

Furthermore, the QUIP technique offers the potential for spectral multiplexing, thereby allowing for the detection of multiple targets per reaction by using a different optical (e.g., fluorescent) signal associated with the presence of each particular target. Finally, in some instances, the primers and probes (e.g., quencher probe or signal probe) can include a label (e.g., a covalently bound fluorescent label, a covalently bound dye, a covalently bound particle, or a covalently bound quencher label) that is amenable to storage in dried form at ambient temperature, which can be difficult with the use of STYO dyes.

One exemplary embodiment of the QUIP technique is illustrated schematically in FIG. 1A. In this instance, the QUIP technique relies upon using a labeled primer. For instance, for LAMP, either the outer primers 10 (F3 or B3), the loop primers 11 (LoopF and LoopB), and/or the inner primers 12 (FIP or BIP) are suitable, and one or more of these primers can be labeled with a fluorescent label (e.g., a fluorophore at the 5'-terminus). As amplification proceeds, the fluorophore-labeled primers are incorporated into the amplicon.

Also included is a short quench probe 13 (e.g., having a length of about 10 to 15 nucleotide), in which the quench probe has a nucleic acid sequence having sufficient complementarity to a portion of a primer. As seen in FIG. 1A, the quench probe 13 has sufficient complementarity to a portion of an inner primer 12. The quench probe includes a quencher label, and one of the primers 12 includes a fluorescent label. These labels are configured to be in sufficient proximity to allow for FRET (Förster resonance energy transfer) when the quench probe hybridized to the inner primer. In one instance, the quencher label is operably linked to the 3'-terminus of the quench probe, and the fluorescent label (or fluorophore) is operably linked to the 5'-terminus of the primer. In one instance, the quench probe is modified at the 3'-terminus with a dark quencher (e.g., Iowa Black® or Black Hole Quencher® labels).

To begin the QUIP method, the primers (e.g., outer primers 10, loop primers 11, and inner primers 12, in which the loop primers are beneficial but only optional) and the probe (e.g., the quench probe 13, generally in excess of the concentration of at least one primer) are combined with a sample including a sample nucleic acid 14. In addition, one or more reagents 15, such as LAMP reagents (for a target DNA) or RT-LAMP reagents (for a target RNA), are included in the mixture. The mixture can be incubated for any useful time (e.g., about 20 to about 60 minutes) at any useful temperature (e.g., from about 60° C. to about 65° C.) to promote amplification.

In one particular instance, the melting temperature T. of the quenching probe complexed to the labeled primer is well below the temperature of the LAMP amplification (e.g., typically 60° C. to 65° C.), such that during the amplification the quenching probe is dissociated and does not participate in or inhibit the reaction.

At a defined endpoint (e.g., after about 30-45 minutes of incubation), the reaction is stopped and cooled down. Upon cooling, any "free" primer that has not been incorporated into an amplicon hybridizes with the quench probe, resulting in direct contact between the fluorophore and the quencher. If the target nucleic is not present or is undetectable 16, then the reaction mixture remains "dark" because unused labeled primers will have hybridized to quench probes to form a duplex 18 of quenched, unused primers. However, if the target nucleic acid is present 17, then the primers will be incorporated into an amplicon. If the primer includes a fluorescent label, then the resultant amplicon will be labeled 19 and detectable as being "bright." The quench probes may hybridize to any unused primers to form a duplex 18, but the labeled amplicon 19 will still be detectable as this amplicon is unavailable to the quenching probe. By virtue of the high rate of DNA synthesis in LAMP, a successful amplification results in a high degree of incorporation of labeled primers into an amplicon, and thus a high residual fluorescence. We have found the fluorescence sufficiently strong that it can be observed by eye in a dimly lit room, using a simple LED keychain and a colored plastic film acting as an emission filter. By combining multiple primers with different fluorophores specific for different targets, multicolor detection can be achieved. For simple eye-based detection, the limitation in multiplexing is likely three to four targets, based on the ability of the human eye to distinguish colors, versus the relatively broad emission spectra of fluorophores. A simple spectrally resolved detector (e.g., resolving fluorescence emission with a prism across a CCD camera) may allow higher order multiplexing.

Of techniques reported in literature, one approach uses dye labeled primers (different dyes for different targets) followed by analysis on a gel. This approach requires opening the tube and performing a post-reaction analysis and requires a multicolor gel scanner.

Another approach includes the "DARQ" technique, which is a real-time detection technique based on displacement of a quencher bound to the 5' end of one of the inner primers (FIP or BIP) (see, e.g., Tanner N A et al., "Simultaneous multiple target detection in real-time loop-mediated isothermal amplification," *Biotechniques* 2012 August; 53(2):81-9). In one instance of the DARQ technique, the quencher probe is significantly longer (~20 bases) and is pre-hybridized to the inner primer and remains bound during the reaction. The presence of the quench probe bound to the inner primer results in a significant inhibition (slowing) of the reaction. To overcome this inhibition, the inner primer:quencher pair must be used in reduced concentrations, such as conditions in which the fluorophore-labeled primer is present as 50% or less of total primer. This lowers the overall signal intensity that can be achieved. By contrast, in the QUIP technique described herein, the quencher is dissociated during the reaction, resulting in minimized inhibition of the reaction, even when using 100% fluorophore-labeled primer, resulting in the maximum possible fluorescence intensity.

We have demonstrated the QUIP technique for two targets: MS2 (an RNA phage) using a FAM-label (fluorescein amidite) on the FIP primer or a Cy®3-label on the LoopF primer (demonstrating the feasibility of using either inner primers or loop primers for QUIP), and also for West Nile Virus (WNV) using a ROX-label (6-carboxyl-X-rhodamine) on the FIP primer. We have developed guidelines for successful design of the fluorophore and quencher combinations, related to the formation of hairpin structures in the primers, and the melting temperature of the quencher:primer complex.

Figure 6:
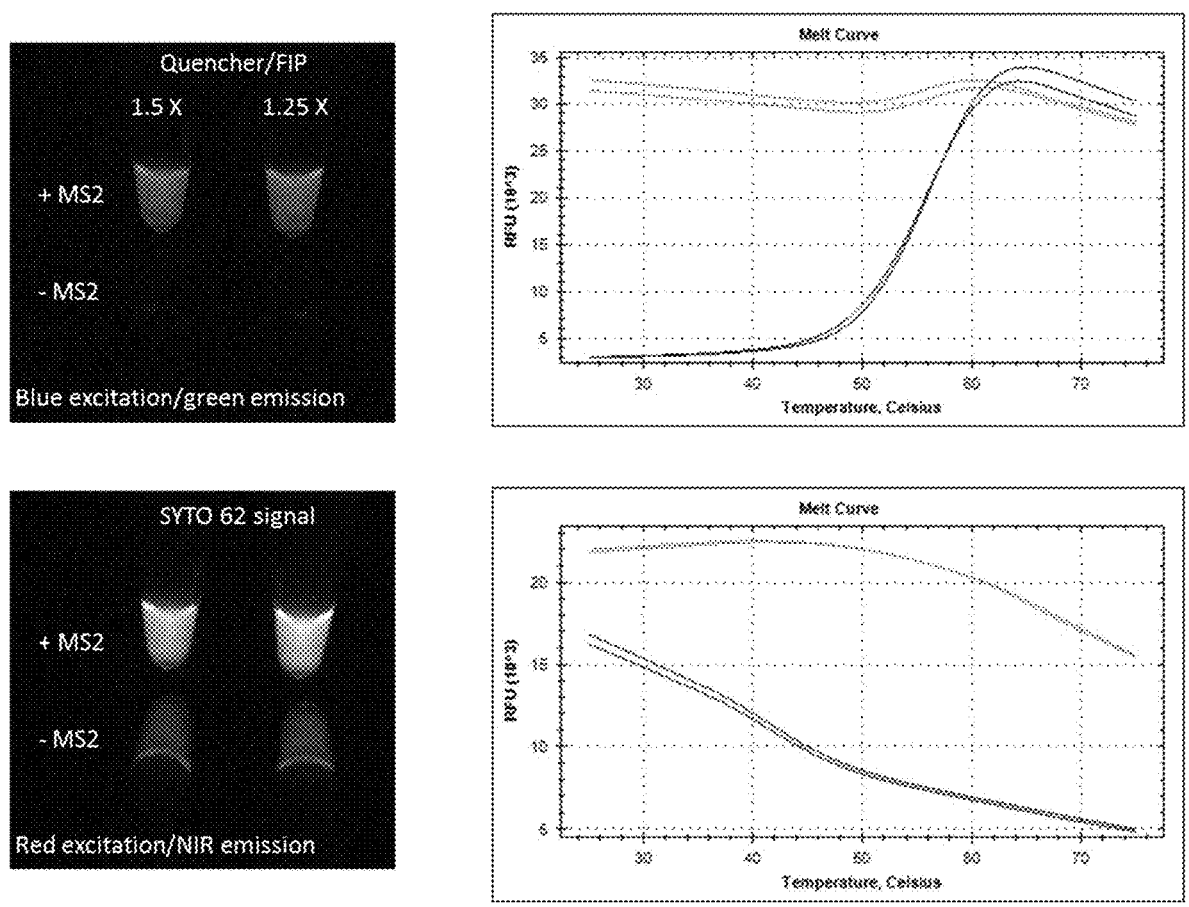
FIG. 6 shows use of an exemplary QUIP technique for detection of bacteriophage MS2. The images at left show a set of reactions with or without the target (+MS2 or −MS2). The top left image shows QUIP detection employing a FAM-labeled FIP primer (1.6 µM total concentration) and two different concentrations of a complementary 13mer quencher (1.25X=2.0 µM; 1.5X=2.4 µM). The top left image was taken with blue LED excitation and a green bandpass filter to detect fluorescence from the FAM-labeled primer. The reactions were independently monitored with the intercalating dye SYTO® 62, which is excited with red light and emits in the far red/NIR. The bottom left image shows the SYTO® 62 reactions, which are illuminated with a red LED and infrared filter. To maximize the difference between the positive and negative reactions, the tubes were heated to approximately 65° C. The graphs to the right are annealing curves generated for these reactions using a real-time PCR instrument, detecting the FAM and SYTO62 channels separately. In each graph, the green curves correspond to the +MS2 reactions, and the blue curves correspond to −MS2 reactions. For the QUIP technique (top right graph), comparing the positive and negative reactions in the FAM channel (green and blue curves) provided an approximately 10-fold difference in signal when observed at 25° C. For the SYTO® technique (bottom right graph), the maximum difference in signal from the SYTO® 62 channel was approximately 3-fold at 60° C., and this drops to approximately 1.4-fold at 25° C.
Figure 7:
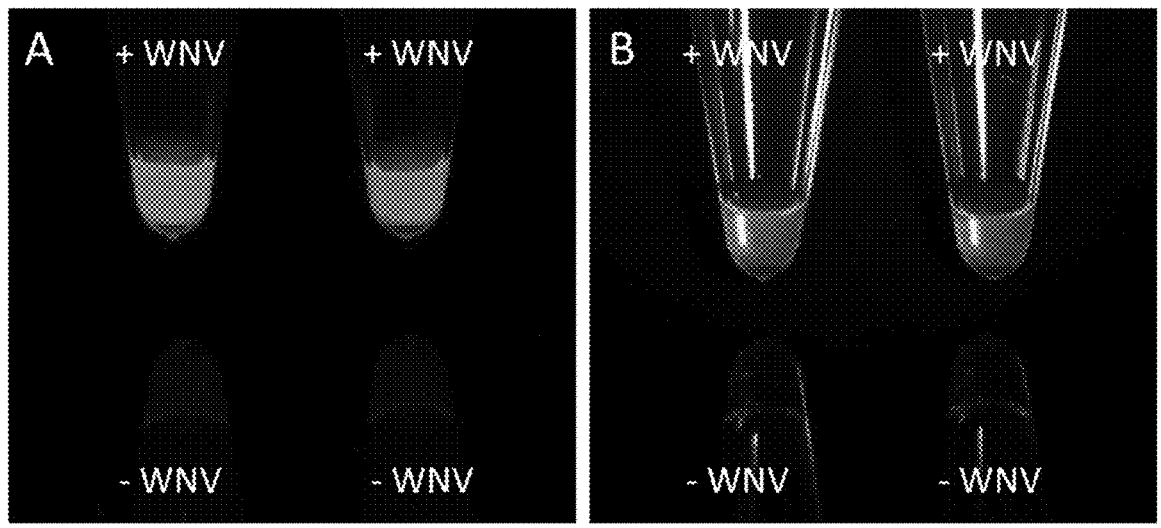
FIG. 7 shows detection of West Nile Virus (WNV) RNA (10 plaque-forming-unit equivalent) by RT-LAMP using ROX-labeled FIP primer and complementary quencher. The un-optimized reaction took 1.5-2 hours, which can be optimized (e.g., by redesigning the quencher) to reduce the reaction time. Panel (A) was taken using a green LED with high-quality excitation and emission filters on the light source and camera. Panel (B) is the same reactions imaged using a handheld green LED flashlight and an inexpensive color gel filter (LEE filter #113; ~$2 per square foot).

Exemplary assays are shown in FIG. 6-8. FIG. 6 shows detection of MS2 using either the QUIP technique with a labeled FIP primer (top image and graph) or the standard technique using an intercalating dye (bottom image and graph). As can be seen, at room temperature (about 25° C.), the QUIP technique provides a greater signal difference between positive and negative results, which corresponds to better signal discrimination. As can be seen, the QUIP technique (FIG. 6, top right graph) clearly provides much better discrimination, particularly at room temperature, which is most convenient for endpoint monitoring.

FIG. 7 shows detection of WNV RNA, which can be visually inspected with laboratory-quality equipment (panel A) or with an inexpensive flashlight and colored filter (panel B). This discernable endpoint detection with simplified equipment provides a promising avenue for point-of-care detection.

FIG. 8 shows MS2 detection using the QUIP technique with a labeled loop primer. As can be seen, any useful primer (e.g., outer, inner, and/or loop primers) can be employed to include the fluorescent label. Use of the quench probe provides a discriminating signal between no target and a sample including the target.

Furthermore, the QUIP technique can be adapted for multiplexed detection, in which different primers are configured to detect different target nucleic acids or different portions of the same target nucleic acid. Each primer specific for a particular sequence can include a different fluorescent label. Since the fluorophore and quencher do not interfere with amplification, we also expect the technique to be amenable to multiplexing with multiple colors for each label. For simplified optical detection, this multiplexed QUIP technique can allow for naked-eye detection using blue and green LEDs to detect products with green and red emission, respectively.

Example 2

Analysis of LAMP Reactions by Quenching of Unincorporated Primers (QUIP)

The present invention is quite broadly applicable to detecting any bacterial, viral, fungal, or protozoan pathogen. Examples of detectable pathogens include but are not limited to: Zaire ebolavirus (EBOV), West Nile Virus (WNV), Chikungunya Virus (CHIKV), Western Equine Encephalitis Virus (WEEV), St. Louis Encephalitis Virus (SLEV), Dengue Virus (DENV), *E. coli* O157:H7, *E. coli* O104:H4, *E. coli* O121:H19, *Salmonella, Listeria, Campylobacter*, and bacteriophage (e.g., MS2 phage). Of these targets, the primer sets used for EBOV, WEEV, SLEV, and MS2 phage are novel (designed and tested in-house), whereas the primer sets for the other targets are adapted from sets reported in open literature.

The present invention is also expected to be readily extended to pathogens related to those for which we have already demonstrated the QUIP detection technique. For example, other filoviruses including Marburg virus (MARV), Sudan ebolavirus (SUDV), and Bundibugyo virus (BDBV); other Flaviviridae including Yellow Fever Virus (YFV), Japanese Encephalitis Virus (JEV), and Hepatitis C virus (HCV); other new-world alphaviruses such as Eastern Equine Encephalitis Virus (EEEV) and Venezuelan Equine Encephalitis Virus (VEEV); and other old-world alphaviruses such as Sindbis virus (SINV) and Ross River virus (RRV). Furthermore, given the demonstrated applicability across a diversity of families of RNA viruses, we expect applicability to other positive-sense and negative-sense RNA viruses not specifically listed here, including Orthomyxoviridae (e.g., influenza viruses), Bunyaviridae (e.g., *hantavirus*, Rift Valley Fever virus, and Crimean-Congo hemorrhagic fever virus), Arenaviridae (e.g. Lassa Fever virus), Caliciviridae (e.g., norovirus). The ability to multiplex two or more targets with distinct spectral emission allows the technique to be used for syndromic panels, e.g., for hemorrhagic fever viruses, or viral encephalitis. Potential applications include rapid detection of viruses for clinical or veterinary medicine, or biosurveillance from human, animal, or environmental samples.

Similarly, for bacteria, the demonstration with multiple genes of *E. coli, Salmonella*, and *Campylobacter* suggest broad applicability across Gram-negative bacteria, including functional genes such as virulence determinants and drug resistance determinants, in addition to species-specific markers. The demonstration with *Listeria* also shows broad applicability to Gram-positive bacteria, including species markers as well as virulence determinants. The ability to multiplex two or more targets with distinct spectral emission allows the technique to be used for syndromic panels, e.g., for diarrheagenic bacteria, or for detection of pathogens in food or environmental samples. Further, we anticipate utility with other pathogens with a DNA genome, including DNA viruses, fungi, and protozoa (e.g., Plasmodium parasites).

In addition, we have now demonstrated that the QUIP technique works in the presence of clinical sample matrices including whole blood, blood serum, red blood cells, stool, urine, and saliva. We have also demonstrated that the technique is compatible with "direct" amplification (without a DNA or RNA extraction step) of viral and bacterial targets, and that the detection technique does not result in any loss of sensitivity, specificity, or speed relative to non-specific detection with an intercalating dye.

FIG. 9 demonstrates endpoint detection of Ebola virus (EBOV) RNA using the QUIP technique. The figure shows endpoint fluorescence images for 5 positive control and 5 negative control reactions, employing the quenched-primer approach for detection. The approach was demonstrated here for 3 novel primer sets targeting 3 different regions of the EBOV genome (GP, VP30, and L genes). In each case, one of the loop primers was labeled. Of the three primer sets, the GP set appears to be superior, with detection of 100 copies of EBOV RNA in less than 15 minutes. All three primer sets were designed to target regions that are conserved between both the original 1976 outbreak of EBOV (Mayinga strain, e.g., GenBank No. AF272001.1, Zaire Ebola virus strain Mayinga, complete genome (18959 bp, RNA); GenBank No. KC242791.1, Zaire ebolavirus isolate EBOV/H.sapiens-tc/COD/1977/Bonduni, complete genome (18959 bp, cRNA); or GenBank No. KC242801.1, Zaire ebolavirus isolate EBOV/H.sapiens-tc/COD/1976/deRoover, complete genome (18959 bp, cRNA), each of which is incorporated herein by reference in its entirety), and publicly available sequences derived from the 2014 EBOV outbreak (collected from Genbank, as of October, 2014; or, e.g., GenBank No. KJ660346.2, Zaire ebolavirus isolate H.sapiens-wt/GIN/2014/Makona-Kissidougou-C15, complete genome (18959 bp, cRNA); GenBank No. KJ660347.2, Zaire ebolavirus isolate *H.sapiens*-wt/GIN/2014/Makona-Gueckedou-007, complete genome (18959 bp, cRNA); or GenBank No. KJ660348.2, Zaire ebolavirus isolate H.sapiens-wt/GIN/2014/Makona-Gueckedou-005, complete genome (18959 bp, cRNA), each of which is incorporated herein by reference in its entirety). This strategy allows us to test the primers with readily available EBOV RNA (from the 1976 Mayinga strain), while also improving the probability that the primers will be effective when tested with samples from the 2014 outbreak. Previously reported RT-LAMP primers for EBOV were not designed to detect the 2014 outbreak strain(s), and consequently may not detect it with sufficient sensitivity for diagnostic applications.

Figure 10A:
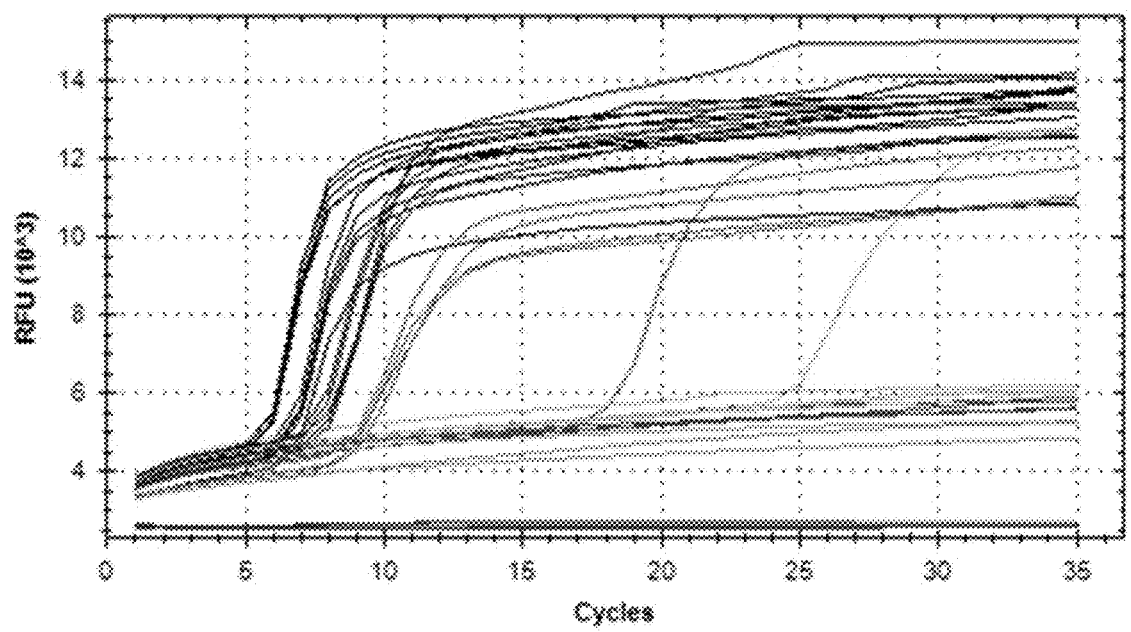
FIG. 10A-10C shows single cell sensitivity for detection of *E. coli* O157:H7. The detection limit of targets cells in whole blood was determined for (FIG. 10A) a standard assay including an intercalating SYTO® 9 dye and (FIG. 10B, FIG. 10C) a QUIP assay using a Cy5 probe and a quench probe. In (FIG. 10C), data are provided for positive detection in each of the five samples (0/5 to 5/5) for the number of O157:H7 cells in each sample (top row, from $10^4$ cells to 1 cell per 10 µL reaction volume, a control O121 cell, and no cell) and for a sample including buffer or 10% whole blood (WB). Data were obtained using either 4 µL loading (plates) or 0.7 µL loading (disks).
Figure 10B:
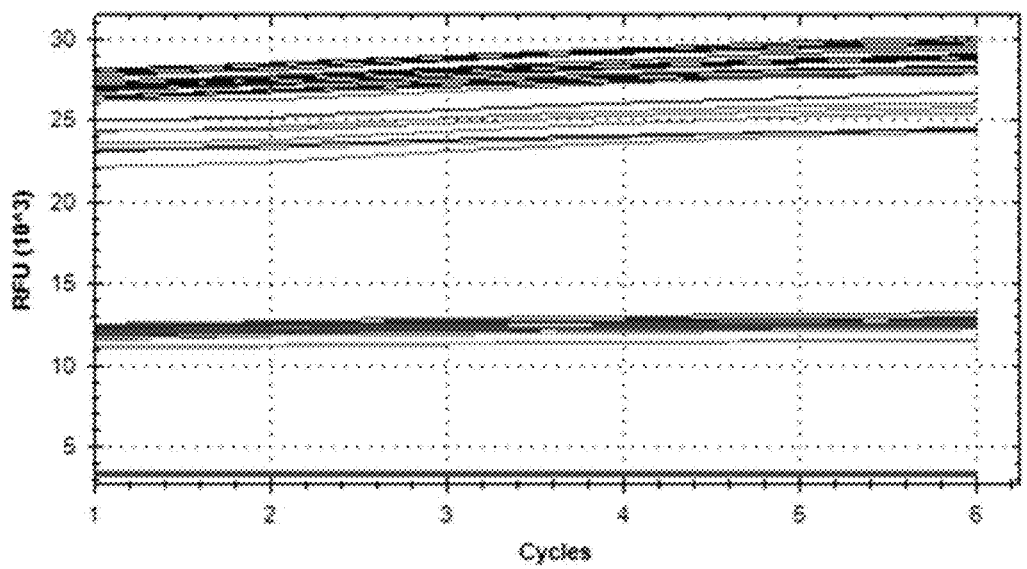
Figure 10C:
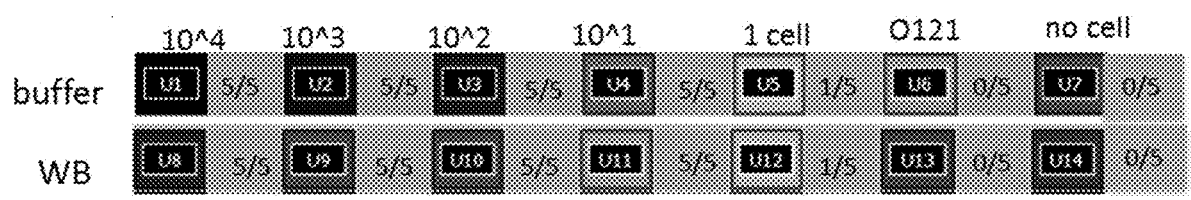

Using the QUIP assay, FIG. 10B-10C illustrates highly sensitive detection of bacteria (10 cells), with no loss in sensitivity despite the presence of 10% whole blood (WB) in the reaction. In contrast, as seen in FIG. 10A, a standard assay using an intercalating dye (SYTO® 9) provides inconsistent detection at low cell concentrations, as well as reduced signal for samples including 10% WB.

Figure 11:
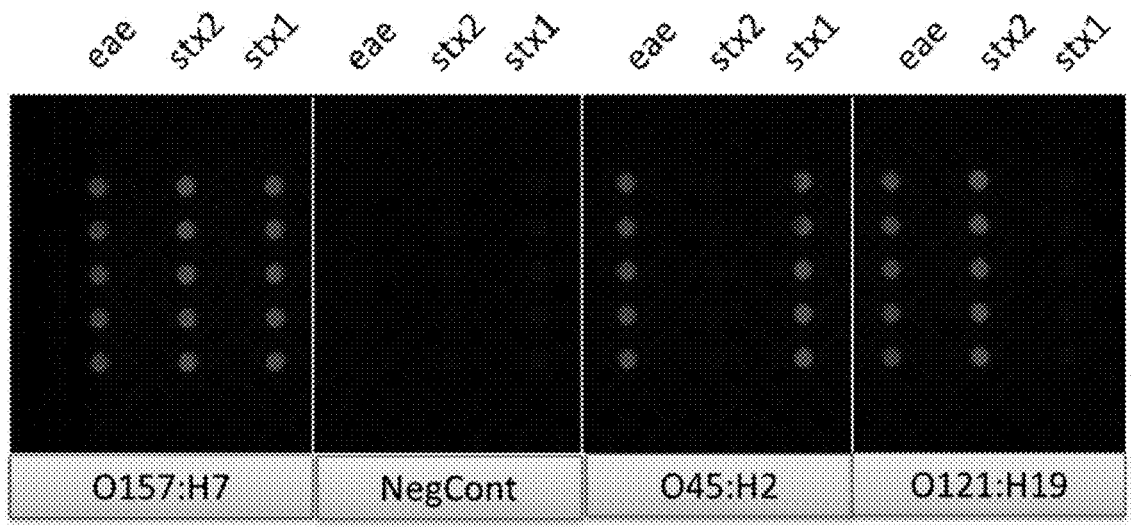
FIG. 11 shows multiplexed detection of Shiga toxin related genes in different serotypes of pathogenic *E. coli* (O157:H7, O45:H2, and O121:H19 serotypes).

FIG. 11 shows application of the QUIP technique to multiple genes for differentiating serotypes of Shiga-toxigenic *E. coli* (STEC). As can be seen, multiplexed detection is possible to detect the presence of various combinations of genes (i.e., eae, sbx2, and six1 genes) in different *E. coli* serotypes. As can be seen, multiplexed detection can be employed using the methods described herein and, e.g., can be employed for identifying particular types and combinations of pathogens.

Example 3

Quenching of Unincorporated Amplification Signal Reporters (QUASR) in RT-LAMP Enables Bright, Single-Step, Closed-Tube, and Multiplexed Detection of RNA Viruses Abstract: Reverse-transcription loop-mediated isothermal amplification (RT-LAMP) has frequently been proposed as an enabling technology for simplified diagnostic tests for RNA viruses. However, common detection techniques used for LAMP and RT-LAMP have drawbacks, including: poor discrimination capability, inability to multiplex targets, high rates of false positives, and (in some cases) the requirement of opening reaction tubes post-amplification. Here, we present a simple technique that allows closed-tube, target-specific detection, based on inclusion of a dye-labeled primer that is incorporated into a target-specific amplicon if the target is present. A short, complementary quencher hybridizes to unincorporated primer upon cooling down at the end of the reaction, thereby quenching fluorescence of any unincorporated primer.

Our technique, which we term QUASR (for Quenching of Unincorporated Amplification Signal Reporters, read "quasar"), does not significantly reduce the amplification efficiency or sensitivity of RT-LAMP. Equipped with a simple LED excitation source and a colored plastic gel filter, the naked eye or a camera can easily discriminate between positive and negative QUASR reactions, which produce a difference in signal of approximately 10:1 without background subtraction. We demonstrate that QUASR detection is compatible with complex sample matrices such as human blood, using a novel LAMP primer set for bacteriophage MS2 (a model RNA virus particle). Furthermore, we demonstrate single-tube duplex detection of West Nile virus (WNV) and chikungunya virus (CHIKV) RNA. Additional details follow.

Introduction

Loop-mediated isothermal amplification (LAMP) is an isothermal nucleic acid amplification technique that is a useful alternative to polymerase chain reaction (PCR) for low-cost or point-of-care diagnostics for infectious disease. The technique can be coupled with reverse transcription (RT-LAMP) for detection of RNA targets, e.g. RNA viruses (see, e.g., Notomi T et al., "Loop-mediated isothermal amplification of DNA," *Nucleic Acids Res.* 2000 Jun. 15; 28(12):e63 (7 pp.); and Parida M et al., "Real-time reverse transcription loop-mediated isothermal amplification for rapid detection of West Nile virus," *J. Clin. Microbiol.* 2004 January; 42(1):257-63).

LAMP (and RT-LAMP) is generally regarded as highly specific and highly sensitive, but a major challenge for LAMP in point-of-care applications is the detection of amplification without requiring cumbersome manipulations or elaborate instrumentation. Furthermore, the available detection mechanisms used in LAMP are not easily amenable to multiplexing to distinguish multiple targets in a single reaction, e.g., for syndromic panels or variant strains of pathogens. In contrast, spectral multiplexing techniques exist for PCR that enable detection of 2-4 targets per reaction (e.g., TaqMan®, Thermo Fisher Scientific). One of our aims was to develop a single-step, closed-tube, and multiplexable detection method for use with LAMP and/or RT-LAMP.

Detection of amplification in LAMP (or RT-LAMP) occurs either at the reaction endpoint or in real-time (quantitative). We have observed that LAMP and RT-LAMP have a narrower quantitative range than corresponding qPCR or qRT-PCR assays. Furthermore, in a point-of-care setting, endpoint monitoring for a positive or negative result is preferable to quantitation for simplicity of interpretation for non-experts.

Endpoint detection in LAMP is usually accomplished by one of the following techniques: observing turbidity (see, e.g., Mori Y et al., "Detection of loop-mediated isothermal amplification reaction by turbidity derived from magnesium pyrophosphate formation," *Biochem. Biophys. Res. Commun.* 2001 Nov. 23; 289(1):150-4); running product on a gel to observe a banding pattern (see, e.g., Notomi T et al., *Nucleic Acids Res.* 2000 Jun. 15; 28(12):e63 (7 pp.)); adding intercalating dye such as SYBR® Green (see, e.g., Iwamoto T et al., "Loop-mediated isothermal amplification for direct detection of Mycobacterium tuberculosis complex, M. avium, and M. intracellulare in sputum sample," *J. Clin. Microbiol.* 2003 June; 41(6):2616-22) or SYTO® dyes (see, e.g., Njiru Z K et al., "Loop-mediated isothermal amplification (LAMP) method for rapid detection of *Trypanosoma brucei rhodesiense*," *PLoS Negl. Trop. Dis.* 2008 Feb. 6; 2(1):e147 (8 pp.)) to observe a color change and/or fluorescence; adding manganese-quenched calcein to generate fluorescence upon amplification (see, e.g., Tomita N et al., "Loop-mediated isothermal amplification (LAMP) of gene sequences and simple visual detection of products," *Nat. Protoc.* 2008; 3(5):877-82); or adding a colorimetric indicator such as hydroxynaphthol blue (see, e.g., Goto M et al., "Colorimetric detection of loop-mediated isothermal amplification reaction by using hydroxy naphthol blue," *Biotechniques* 2009 March; 46(3):167-72) or pH-sensitive dyes (see, e.g., Tanner N A et al., "Visual detection of isothermal nucleic acid amplification using pH-sensitive dyes," *Biotechniques* 2015 Feb. 1; 58(2):59-68) to generate a color change upon amplification.

Each of these existing techniques has specific advantages and disadvantages. In our experience, the turbidity produced by LAMP is subtle and difficult to see by naked eye. Alternatively, running the product on a gel or post-reaction addition of SYBR® Green requires opening the tube after amplification, which presents a risk for amplicon contamination. While several of the SYTO® family of dyes (notably SYTO® 9, SYTO® 62, and SYTO® 82) are non-inhibitory for closed-tube endpoint or real-time detection, fluorescence observations must be performed at elevated temperature for maximum discrimination between positive and negative amplifications. Manganese-quenched calcein detection is reported to suffer from inhibition from manganese (see, e.g., Goto M et al., *Biotechniques* 2009 March; 46(3):167-72). The color change resulting from hydroxynaphthol blue may be too subtle for some users (particularly those with color vision deficiency) to distinguish without instrumentation. Although the color change from pH-sensitive dyes can be quite striking, this technique relies upon weakly buffered reaction mixtures and may not perform well with crude or buffered samples (e.g., 10% blood or soils). Furthermore, none of these techniques is sequence specific, but rather detect total amplification. These detection methods are thus prone to detection of non-specific amplification, which can occur with LAMP (and other nucleic acid amplification techniques including PCR) even in the absence of the specific target.

The lack of target specificity further means that the above detection techniques cannot be multiplexed to allow detection of more than one target in a single reaction. Several reports describe multiplexing by means of performing a post-reaction restriction digest, and running the product on a gel (see, e.g., Iseki H et al., "Development of a multiplex loop-mediated isothermal amplification (mLAMP) method for the simultaneous detection of bovine Babesia parasites," *J. Microbiol. Methods* 2007 December; 71(3):281-7); this requires opening the tube plus several additional processing steps. A number of other reports describe multiplexing techniques for LAMP or other isothermal strand displacement techniques based on—displacement of a bound quencher (see, e.g., Yi J et al., "Molecular Zipper: a fluorescent probe for real-time isothermal DNA amplification," *Nucleic Acids Res.* 2006 Jul. 5; 34(11):e81 (5 pp.)); fluorescence resonance energy transfer (FRET) (see, e.g., Kubota R et al., "FRET-based assimilating probe for sequence-specific real-time monitoring of loop-mediated isothermal amplification (LAMP)," *Biol. Eng. Trans.* 2011; 4(2):81-100); a combination of labeled primers and intercalating dyes (see, e.g., Kouguchi Y et al., "Homogenous, real-time duplex loop-mediated isothermal amplification using a single fluorophore-labeled primer and an intercalator dye: Its application to the simultaneous detection of Shiga toxin genes 1 and 2 in Shiga toxigenic *Escherichia coli* isolates," *Mol. Cell. Probes* 2010 August; 24(4):190-5); or strand displacement of a quencher bound to a probe targeting the loop region of the amplicon (DARQ) (see, e.g., Tanner N A et al., "Simultaneous multiple target detection in real-time loop-mediated isothermal amplification," *Biotechniques* 2012 August; 53(2):81-9). However, these techniques significantly inhibit the LAMP reaction.

We have developed a novel approach for endpoint determination of LAMP and RT-LAMP reactions, based upon Quenching of Unincorporated Amplification Signal Reporters (QUASR). Our technique is named after the extremely luminous celestial objects known as quasars. Like its namesake, QUASR is capable of producing an extremely bright signal. In this Example, we first outline the operating principles of QUASR. Then, we highlight QUASR's superior endpoint discrimination ability compared to SYTO® dye using bacteriophage MS2 as a model RNA virus. Furthermore, we demonstrate the feasibility of QUASR detection of MS2 in a reaction containing 10% whole blood. Next, we apply QUASR to perform single-tube duplex detection of RNA from two mosquito-borne viruses: West Nile virus (WNV) and Chikungunya virus (CHIKV). Briefly, we spotlight QUASR's excellent resistance to false positives. Finally, we close with a discussion of how QUASR LAMP relates to the previously reported DARQ LAMP technique (see, e.g., Tanner N A et al., *Biotechniques* 2012 August; 53(2):81-9).

Materials and Methods

LAMP primer design: LAMP Designer v1.13 software (Premier Biosoft) was used with default parameters to scan for suitable LAMP primer sets for bacteriophage MS2 (GenBank NC_001417.2). Primer sets were analyzed by BLAST, comparing to all viral sequences in GenBank, to determine likelihood of cross-reactivity with other viruses. Primer sets were also evaluated to minimize hairpin formation and self-dimerization using OligoAnalyzer® and mFold® programs (IDT, Coralville, USA. Retrieved 6 Oct. 2015, idtdna.com/Scitools). The MS2 primer set reported here targets the MS2 replicase (RNA-dependent RNA polymerase) gene, and sequences are shown in Table 1 (in Example 4). RT-LAMP primer sets for WNV and CHIKV were obtained from published literature, and also listed in Table 1 (in Example 4).

Viral templates: MS2 phage was obtained from ATCC (15597-B1) (Manassas, Va.). MS2 phage was diluted in water and used directly in assays, without propagation or extraction of RNA (see, e.g., Ninove L et al., "RNA and DNA bacteriophages as molecular diagnosis controls in clinical virology: a comprehensive study of more than 45,000 routine PCR tests," *PLoS One* 2011 Feb. 9; 6(2): e16142 (7 pp.)). An MS2 RNA standard (United States Biological) was also used in some assays for quantitation. WNV (isolate L-CA-04 SAC-04-7168, GenBank accession no. DQ080059) and CHIKV (strain Ross, GenBank accession no. AF490259) were cultured and quantitated by plaque assay, and RNA was extracted as described in supplementary methods. WNV and CHIKV culture requires biosafety level 3 (BSL-3) containment and protocols. Genomic RNA from positive-sense RNA viruses such as WNV and CHIKV should be treated as potentially infectious material.

QUASR primer design: QUASR primers and their complementary quenching probes were designed using IDT's online OligoAnalyzer tool (v3.1) with parameters adjusted for LAMP reaction conditions. Fluorescently labeled primers for QUASR detection of MS2, WNV, and CHIKV were selected by avoiding primers that were likely to form stable hairpins. The melting temperature of the fluorescent primer-quenching probe complex was designed to be significantly lower than 65° C. (at least 5° C. lower). Primers, dye-labeled primers, and quenching probes were ordered from Integrated DNA Technologies (Coralville, Iowa). Primers and their quenching probe sequences are reported in Table 1 and Table 2 (see Example 4).

RT-LAMP assays: RT-LAMP was performed in 10 µL reaction volumes in thin-walled PCR strip tubes, 96-well plates, or 384-well plates. The reaction mixture had a final composition (after adding water or template) of 1× Isothermal Amplification Buffer (New England Biolabs, NEB #B05375) supplemented with an additional 6 mM $MgSO_4$ (NEB #B1003S, final 8 mM $MgSO_4$), 1.4 mM each dNTP (NEB #N0447L), 0.32 units/µL, Bst 2.0 WarmStart DNA polymerase (NEB #M0538M), 0.2 units/µL, AMV reverse transcriptase (NEB #M0277T, or Life Science Advanced Technologies #AMVRTT-5), and 2 µM (or in some instances without) SYTO® 9, 62, or 82 detection dyes (Life Technologies #S-34854, #S-11344, and #S-11363). In some instances, 0.8 M betaine (Sigma #B-0300) was added to the reactions.

Primers were used in the amounts typically recommended for LAMP: 0.2 µM each for outer primers F3 and B3; 1.6 µM each for inner primers FIP and BIP; and 0.8 µM each for loop primers LF and LB. Quenching probes were typically added at 1.5× the concentration of the corresponding fluorescently labeled primer. Other concentrations were used in experiments as reported in figures.

For RT-LAMP with 10% human blood, 20U of RNase-OUT™ (Thermo Fisher Scientific, MA) and 1 µL of human whole blood (Innovative Research, MI) were added to a final volume of 10 µL reaction containing the RT-LAMP mixture listed above.

RT-LAMP with real-time fluorescence monitoring was carried out in a BioRad CFX96 or CFX384, using detection channels 1 (FAM), 2 (HEX), and 5 (Cy5) for monitoring SYTO® 9, 82, and 62 dyes, respectively. Reactions were incubated at a constant temperature of 63-65° C. for 50-70 minutes, with plate read steps at intervals of 1 minute (in the BioRad CFX96 (CFX384), this is accomplished with a 48-second (38 second) single-temperature cycle followed by a plate read which takes approximately 12 seconds (22 seconds) in all-channel mode). Incubation was typically followed by inactivation of the enzyme at 95° C. for 2 minutes, followed by cooling to 25° C. in 0.1 to 1.0° C. increments. Time-to-positivity values were determined using the Bio-Rad CFX Manager software, using baseline-subtracted curves, and a single threshold value auto-calculated by the CFX manager for SYTO® signal.

Duplexed WNV and CHIKV RNA detection was accomplished by adding both primer sets in at one half their normal concentration. Two to 100 PFU equivalents of each viral RNA was added to the appropriate reactions.

Endpoint images were taken with a color camera (Point Grey Research, #CMLN-13S2C-CS, Richmond, BC) or an iPhone 6 (Apple, Cupertino, Calif.). Fluorescence was excited with a 10 W LED (LEDEngin, Inc. #LZW4, Blue- 465 nm, Green-523 nm, or Red-623 nm). Filters were used for excitation (480/30 BP, 520/40 BP, or 622/36 BP) and emission (535/40 BP, 550 LP, or 620/60 BP) (Edmund Optics, Barrington, N.J.; Chroma Technologies, Bellows Falls, Vt.; or Thorlabs, Newton, N.J.) with the high power LED and color camera. For detection by eye or iPhone 6, an LED flashlight served as the excitation source, and a single layer of plastic lighting gel (LEE Filters, Andover, Hampshire, UK; filter #113 (red), or #158 (green and duplexed)) was used as an emission filter. No image adjustment aside from cropping/rotating was performed.

Results and Discussion

Figure 12:
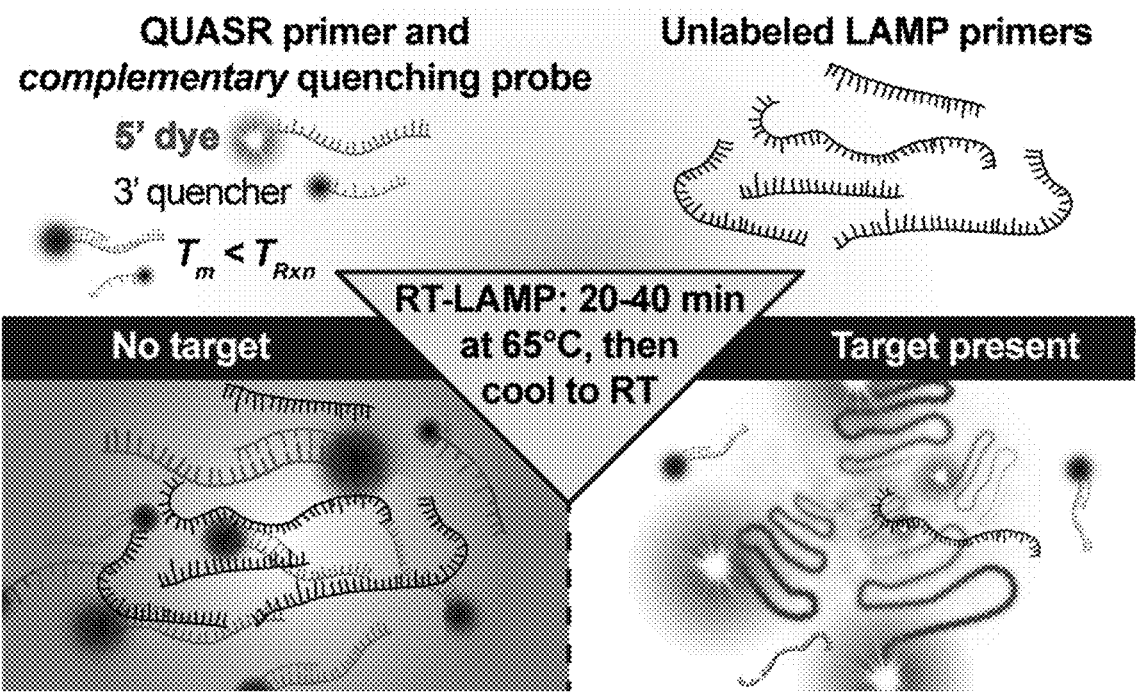
FIG. 12 shows a schematic of one non-limiting embodiment of the principle of QUASR detection in LAMP or RT-LAMP. One of the loop primers (LF or LB), or inner primers (FIP or BIP) is labeled with a dye. The reaction mixture also contains a short probe, labeled with a dark quencher at the 3' end, and complementary to 7-13 bases at the 5' end of the dye labeled primer. The quench probe is present at slight excess relative to the labeled primer and has Tm>10° C. below the temperature of the LAMP reaction, such that it remains dissociated during the amplification. After incubation, the reaction is cooled to ambient temperature, resulting in dark quenching of fluorescent primers (negative reactions), or highly fluorescent amplicons (positive reactions).

We schematically illustrate one non-limiting embodiment of the QUASR technique in FIG. 12. This particular QUASR technique relies upon simply using a primer (for LAMP, either the inner primers FIP or BIP, or the loop primers, LoopF and LoopB are suitable) labeled with a fluorophore at the 5'-end. As amplification proceeds, the fluorophore-labeled primers are incorporated into the amplicon. Also included is a short quencher probe, typically with 7-13 bases complementary to the 5'-end of the labeled primer. The quencher probe is modified at the 3'-end with a dark quencher (e.g., Iowa Black® or Black Hole Quencher®). In one instance, the melting temperature of the quenching probe annealed to the labeled primer (typically <55° C.) must be well below the temperature of the LAMP amplification (typically 60-65° C.), such that during the amplification the quenching probe is dissociated and does not participate in or inhibit the reaction. We have found that a mismatch (e.g., one or more internal mismatches) in the quenching probe can reduce the complex melting temperature while preserving specificity. In addition, base mismatches at the end of a nucleic acid sequence can also be employed to reduce $T_m$.

Figure 13:
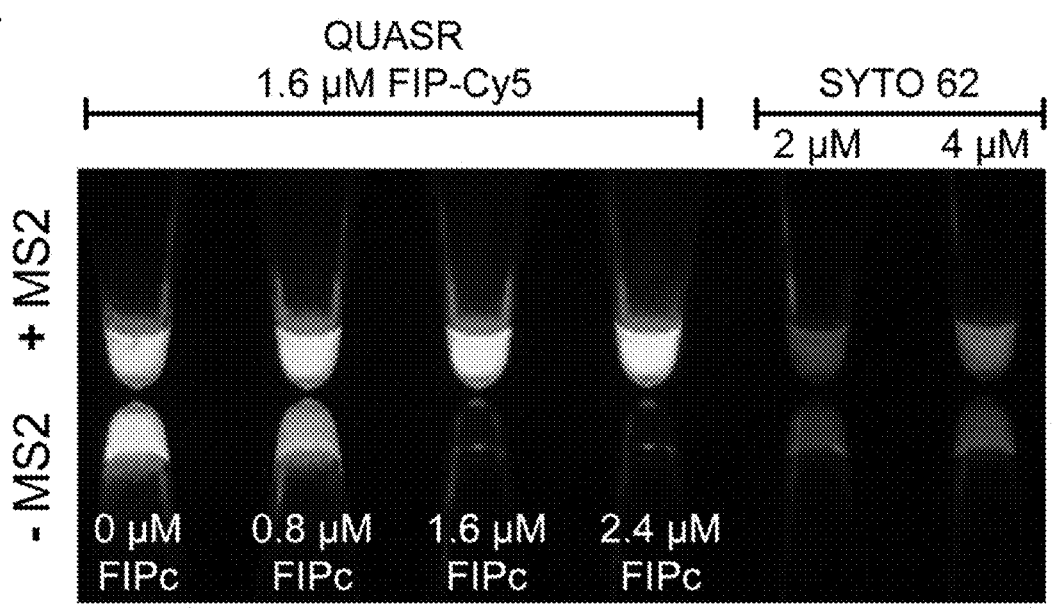
FIG. 13 shows that QUASR improves endpoint discrimination between positive and negative reactions compared to an intercalating dye. A) Comparison of room temperature endpoint detection with QUASR versus the intercalating dye SYTO® 62 for RT-LAMP amplification of MS2 phage (in-house designed primer set) in PCR tubes. The top row of tubes shows positive reactions and the bottom row of tubes shows negative reactions. The 4 reactions on the left utilize QUASR via FIP-Cy®5 with varying amounts of complementary quenching probe, FIPc. It is apparent that fluorescence in negative reactions is strongly quenched with the addition of FIPc probe. Compared to either 2 µM or 4 µM SYTO® 62 (right), 1.6 µM FIP QUASR yields a brighter signal and better discrimination. B) Annealing curves for QUASR (1.6 µM FIP-Cy®5 with 2.4 µM FIPc) and SYTO® 62 (4 µM) reactions post-amplification, by monitoring fluorescence in the Cy®5 channel, while cooling from 85° C. to 25° C. in a real-time PCR machine. With QUASR, the difference between positive and negative samples becomes obvious as the temperature drops below the annealing temperature of the quench probe. C) At room temperature and without background subtraction, the discrimination between positive and negative reactions is 8:1 for QUASR but only minimal for SYTO® 62. With background subtraction (water only controls), QUASR discrimination approaches 700.
Figure 13:
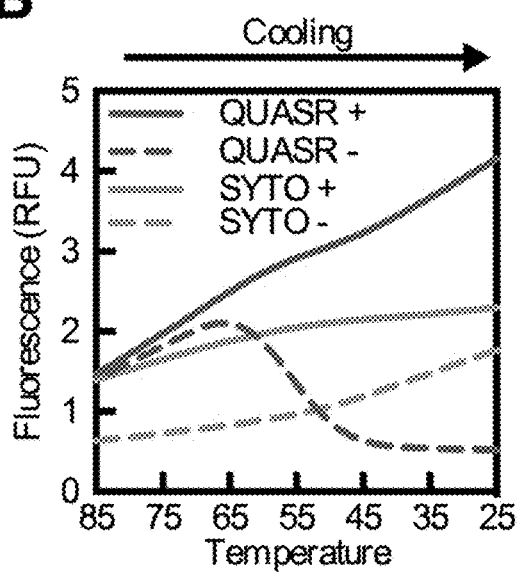
Figure 13:
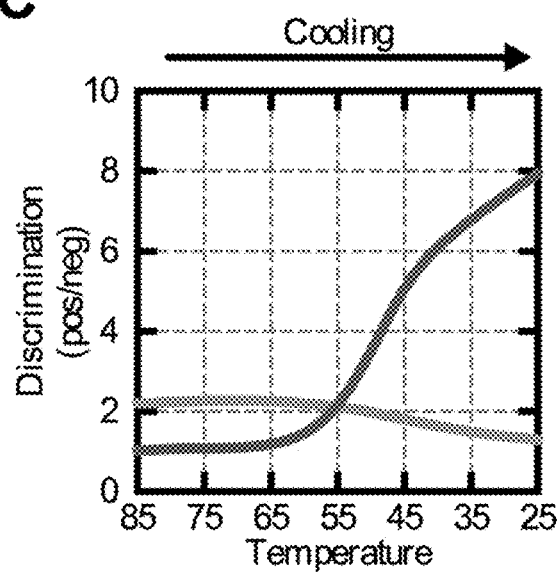

At a defined endpoint (typically 30-45 minutes of incubation), the reaction is stopped, and cooled down. Upon cooling, any free primer that has not been incorporated into an amplicon hybridizes with the quenching probe, resulting in close proximity between the fluorophore and the quencher. However, any labeled primer that has been incorporated into an amplicon is unavailable to hybridize with the quenching probe, and thus remains bright. Excess quenching probe ensures that fluorescence is fully quenched in negative reactions (FIG. 13). Labeled FIP or BIP primer generally provides brighter signal than labeled LoopF or LoopB primer, since the former are used at twice the concentration of the latter in the LAMP reaction, and thus incorporated to higher degree into amplicons.

QUASR at room temperature outperformed SYTO® dyes at endpoint discrimination.

We have previously found the SYTO® family of intercalating dyes (particularly SYTO® 9, SYTO® 82, and SYTO® 62) to be useful for routine closed-tube detection in LAMP because these dyes are non-inhibitory to LAMP at relatively high concentrations of 2-10 µM, thus offering bright signals at a variety of wavelengths. However, thanks to the high degree of DNA synthesis and excess of nucleotides in LAMP, a successful QUASR amplification results in a high degree of incorporation of labeled primers into an amplicon, and thus a high residual fluorescence that allows even clearer discrimination between positive and negative reactions.

We demonstrate this in FIG. 13, using bacteriophage MS2 as a model RNA virus (see, e.g., Ninove L et al., *PLoS One* 2011 Feb. 9; 6(2):e16142 (7 pp.)) for detection by QUASR RT-LAMP. As seen in FIG. 13, the QUASR technique detects amplification optimally at room temperature. The fluorescence from QUASR is sufficiently strong that it can be observed by eye, even indoors with lights on, using a colored LED flashlight for excitation and a colored plastic film (theatre lighting gel) acting as an emission filter. This makes it convenient to use in the absence of specialized equipment.

Figure 14:
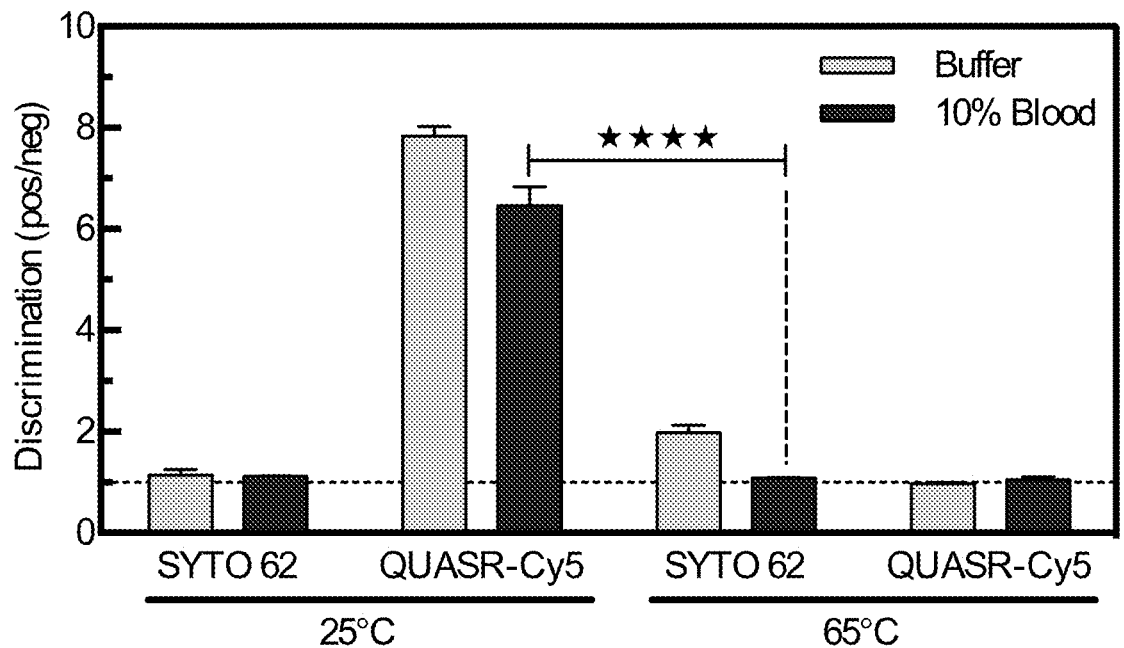
FIG. 14 shows that QUASR enables room temperature discrimination between positive and negative RT-LAMP reactions in 10% whole blood. In contrast, discrimination with SYTO® 62 is completely lost in the presence of whole blood. P<0.0001.

QUASR provides robust detection in the presence of crude sample matrices. In FIG. 14, we show that QUASR detection of MS2 with a Cy®5-labeled primer provides better discrimination than SYTO® 62 in a reaction mixture containing 10% whole human blood. Amplification in the presence of whole blood can be observed by monitoring the SYTO® 62 signal in a real-time PCR machine, with a similar time to positivity as a reaction without blood, meaning that RT-LAMP itself is not strongly inhibited. However, the absolute rise in signal with SYTO® 62 is weak, perhaps due to complexation of the intercalating dye with components in blood. The Cy®5 fluorophore used in QUASR, by contrast, is less sensitive to the presence of blood. Consequently, less sample processing may be required for LAMP or RT-LAMP point-of-care diagnostics or surveillance measurements from materials like soils. Unlike pH sensitive dyes, QUASR remains compatible with these types of crude, buffered samples.

Figure 15:
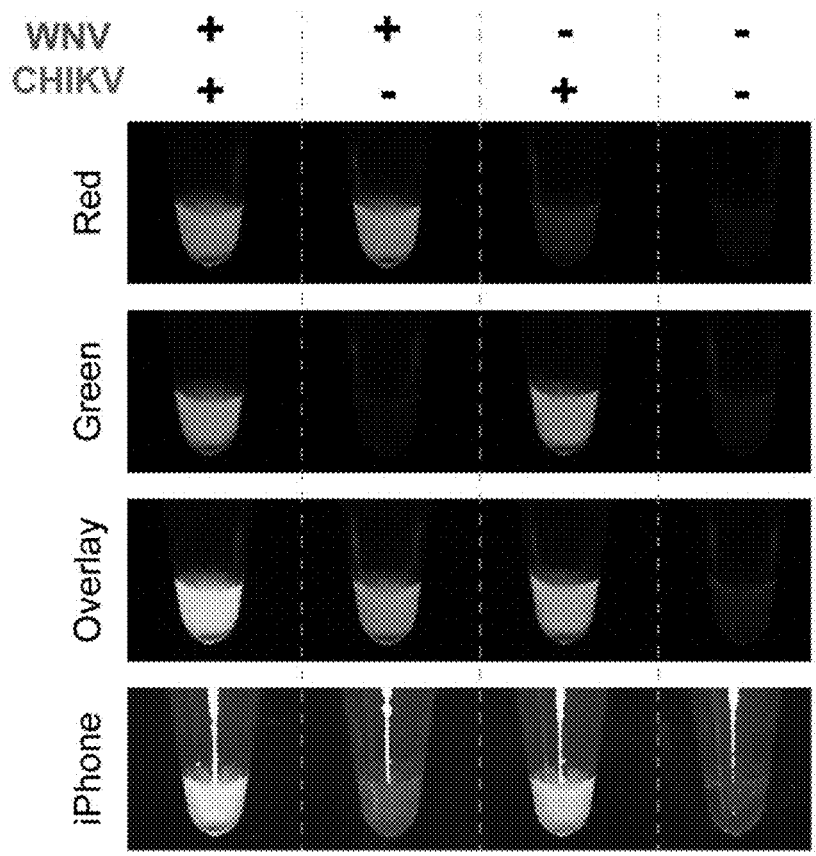
FIG. 15 shows multiplexed visual detection of WNV/CHIKV by QUASR RT-LAMP. 100 PFU equivalent of each viral RNA was used in each reaction. WNV positives appeared bright red when excited with green light, and CHIKV positives appeared bright green when excited with blue light. A composite overlay of the images shows that the combination appears yellow. The unadjusted image from an iPhone 6 using an unfiltered blue LED excitation source and a plastic theater gel as an emission filter confirmed multiplexed detection.

By combining multiple QUASR primer sets specific for different targets, spectrally multiplexed detection can be achieved, as demonstrated in FIG. 15 for WNV and CHIKV. WNV is now endemic to the United States, and regularly affects birds, livestock, and humans, causing severe symptoms and sometimes death (see, e.g., Hayes E B et al., "Epidemiology and transmission dynamics of West Nile virus disease," *Emerg. Infect. Dis.* 2005 August; 11(8):1167-73). CHIKV is an emerging virus globally (see, e.g., Thiboutot M M et al., "Chikungunya: a potentially emerging epidemic?," *PLoS Negl. Trop. Dis.* 2010 Apr. 27; 4(4):e623 (8 pp.)), with autochthonous transmission first reported in the United States in 2014 (see, e.g., Kendrick K et al., "Notes from the Field: Transmission of Chikungunya Virus in the Continental United States—Florida, 2014," *Morbidity and Mortality Weekly Report*, Dec. 5, 2014; 63(48):1137). It causes fever, aches, and chronic pain (see, e.g., Queyriaux B et al., "Clinical burden of chikungunya virus infection," *Lancet Infect. Dis.* 2008 January; 8(1):2-3).

Both WNV and CHIKV viruses are transmitted by mosquito bites and present similar initial symptoms. A multiplexed assay for WNV and CHIKV would be useful for point-of-care diagnostics and vector-borne disease surveillance (see, e.g., Naze F et al., "Simultaneous detection and quantitation of Chikungunya, dengue and West Nile viruses by multiplex RT-PCR assays and dengue virus typing using high resolution melting," *J. Virol. Methods* 2009 December; 162(1-2):1-7). In FIG. 15, the bright red (WNV) and green (CHIKV) fluorescent signals generated by the target-specific QUASR are easily distinguishable from negative reactions. Simultaneous color detection is possible by examining the fluorescence overlay (FIG. 15, third row of images) or exciting fluorescence with a blue LED and observing through an amber-colored gel filter, as captured by a smartphone in FIG. 15 (bottom row of images).

Because of its robustness, simplicity, and ability to multiplex, QUASR RT-LAMP could lower testing costs and expand access to diagnostics and biosurveillance tools. For such applications, discriminating positive from negative at a defined endpoint (e.g., 30 minutes of amplification) to provide a yes-or-no answer is instrumentally simpler than real-time quantitative detection and is simpler for a non-specialist to interpret. In cases where quantitative detection of nucleic acids is desirable, qRT-PCR still outperforms qRT-LAMP, even when using refined methods (see, e.g., Sun B et al., "Mechanistic evaluation of the pros and cons of digital RT-LAMP for HIV-1 viral load quantification on a microfluidic device and improved efficiency via a two-step digital protocol," *Anal. Chem.* 2013 Feb. 5; 85(3):1540-6). Nevertheless, we note that one can combine QUASR with real time monitoring with intercalating dyes, such as SYTO® 9, 62, or 82, to achieve uninhibited real time detection with a subsequent screen for false positives by endpoint detection with QUASR. This makes QUASR particularly useful for surveillance of rare viruses, for which true positive rates are similar to rates of false positives by SYTO® dye detection.

The origins of nonspecific amplification in LAMP are complex, and different primer sets are susceptible to this phenomenon to different degrees. We cannot rule out that the labeled primer could participate in nonspecific amplification reactions in some circumstances, which could prevent post-reaction quenching by QUASR. However, we have observed that primer sets that occasionally give rise to positive signals in no-template control reactions monitored with an intercalating dye (which include the WNV and MS2 primer sets used in this study), rarely give rise to false positives with the QUASR technique (Table 3, see Example 4). A detailed examination of this phenomenon, across many primer sets, can provide further guidance, but we note cautiously that the QUASR technique appears more resistant to false positive detection than non-specific techniques, such as intercalating dyes, turbidity, quenched calcein, or pH-sensitive dyes.

Figure 16:
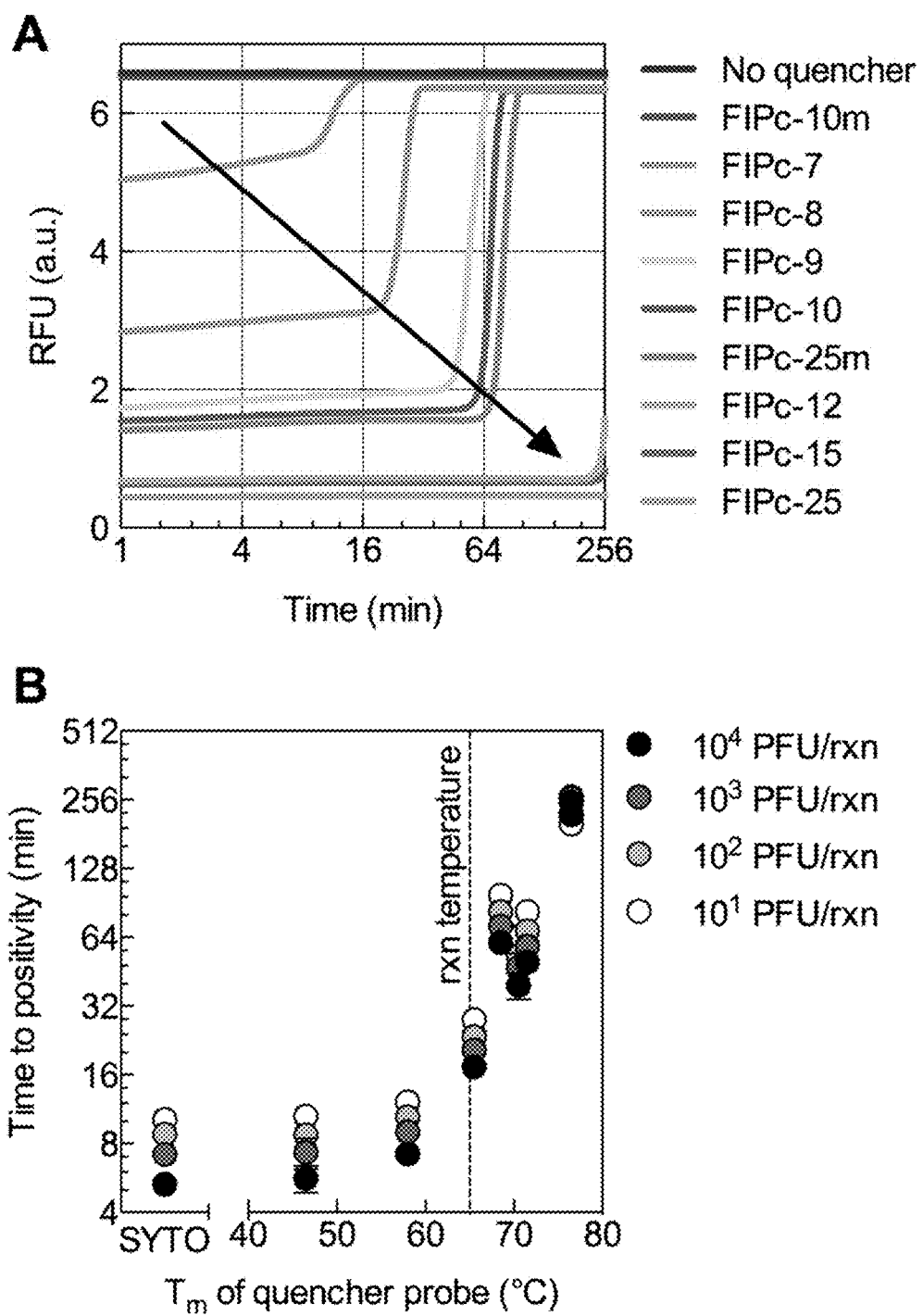
FIG. 16 shows that QUASR LAMP and DARQ LAMP exist on a continuum. A) Real-time fluorescence detection of 10,000 PFU equivalent WNV RNA per 10 μL reaction by RT-LAMP. Increasing the melting temperature of the FIP-complementary quencher probe decreases background fluorescence but dramatically slows amplification time. The arrow demonstrates the transition from QUASR RT-LAMP to DARQ RT-LAMP, represented by the full-length quenching probe FIPc-25. B) The time to positivity increases dramatically as the FIP/FIPc complex melting temperature approaches and surpasses the reaction temperature for RT-LAMP. Melting temperature is far more important than even a 1,000-fold change in WNV template RNA concentration.

The acronym "QUASR" suggests a relationship to black holes and, by connotation, to darkness. Indeed, the previously described DARQ (see, e.g., Tanner N A et al., "Simultaneous multiple target detection in real-time loop-mediated isothermal amplification," *Biotechniques* 2012 August; 53(2):81-9) technique exists on a continuum with our new QUASR technique (FIG. 16). In both the QUASR and DARQ techniques, fluorescent signal arises from a dye-labeled incorporating primer and complementary quencher (the converse arrangement is also reported for DARQ, see, e.g., Tanner N A et al., *Biotechniques* 2012 August; 53(2): 81-9).

In contrast to DARQ LAMP, however, QUASR LAMP is non-inhibitory and brighter, but provides endpoint detection only. The key difference is that in the DARQ technique, a full-length complementary quencher is used, which is hybridized to the incorporating primer prior to the start of the reaction and must be displaced during the course of amplification to generate a signal. Although this approach allows real-time monitoring of the reaction, the presence of the bound quencher dramatically inhibits the reaction.

As we demonstrate in FIG. 16, QUASR and DARQ exist on a continuum determined by quenching probe Tm. In Tanner N A et al., *Biotechniques* 2015 Feb. 1; 58(2):59-68, the authors typically use a 50:50 mixture of labeled and unlabeled primer to reduce the degree of inhibition, but which also diminishes the intensity of the signal. In our hands, using the DARQ technique with several targets requires an even lower ratio of labeled to unlabeled primer for optimal speed, but this resulted in further reduced signal intensity. Because QUASR uses shorter quench probes that are dissociated at the temperature of the reaction, inhibition is negligible, and the fluorescently labeled primers can be used at full strength.

We also note that Curtis et al. reported use of full-length quenchers complementary to a labeled loop primer, for RT-LAMP detection of HIV (see Curtis K A et al., "Rapid detection of HIV-1 by reverse-transcription, loop-mediated isothermal amplification (RT-LAMP)," *J. Virol. Methods* 2008 August; 151(2):264-70). As noted above, use of a full-length quencher significantly inhibits the amplification, and thus the technique of Curtis et al., while similar in principle to QUASR, requires opening the tube to add the quencher at the conclusion of the reaction. This adds an extra step to the procedure, and (like any open-tube method) adds the risk of amplicon contamination of the laboratory. Curtis et al. do note that their approach, like QUASR, eliminates false positives resulting from the non-specific amplification that occasionally occurs in LAMP, supporting the observation that the dye-labeled primers are not incorporated to a high degree in non-specific amplification products.

Conclusion

QUASR enables non-inhibitory, bright, single-step, closed-tube, and multiplexed detection of DNA and RNA targets with LAMP and RT-LAMP. The specific duplex demonstrated here would offer, for example, the opportunity for a portable "field test kit" to detect the presence of both WNV (currently endemic across the continental USA) and CHIKV (currently a worldwide epidemic, and currently emerging in the southeastern USA) in field-caught mosquitoes. Furthermore, QUASR is compatible with complex sample matrices, such as blood, and requires no specialized equipment to observe reaction endpoints. We have applied the QUASR technique to numerous other bacterial and viral targets, with similar performance to that described here for MS2, WNV, and CHIKV. Combined with the general tolerance of LAMP and RT-LAMP to crude samples, we anticipate that QUASR will be an enabling technology for simple, rapid detection of nucleic acid targets.

Example 4

Experimental Information for QUASR

Primer and quencher sequences; viral culture methods; characterization of RT-LAMP primer set for MS2 phage; and reduction of false positives by QUASR RT-LAMP are described in this Example.

Primer and Quencher Sequences

The sequences of primers used for RT-LAMP detection of MS2, WNV, and CHIKV are provided in Table 1. The present invention encompasses a primer including a nucleic acid sequence that is substantially identical (e.g., has at least about 90% sequence identity) to any one of SEQ ID NOs:1 and 10-14 and having an optional label (e.g., a fluorescent label at the 3'- or 5'-terminus).

TABLE 1

RT-LAMP primers

| Primer Name | Genome position[c] | Sequence | SEQ ID NO: |
|---|---|---|---|
| MS2 F3 | 2520-2539 | CTTGCGACGATAGACTTATC | 10 |
| MS2 B3 | 2776-2759 | TAGATGCCTATGGTTCCG | 11 |
| MS2 FTP | 2658-2638 (F1c) | ATCGTATCGTCTCGCCATCTACCACCAG | 1 |

TABLE 1 -continued

RT-LAMP primers

| Primer Name | Genome position[c] | | Sequence | SEQ ID NO: |
|---|---|---|---|---|
| (F1c + F2) | 2586-2607 | (F2) | AGCTATATTCATATC | |
| MS2 BIP (B1c + B2) | 2673-2693 2739-2722 | (B1c) (B2) | ACAATGGGAAATGGGTTCACAGGGTC GCTTTGACTATTG | 12 |
| MS2 LF | 2636-2619 | | GATTCCGTAGTGTGAGCG | 13 |
| MS2 LB | 2699-2720 | | GCTAGAGTCCATGATATTCTGG | 14 |
| WNV F3[a] | 1028-1046 | | TGGATTTGGTTCTCGAAGG | 15 |
| WNV B3[a] | 1228-1210 | | GGTCAGCACGTTTGTCATT | 16 |
| WNV FIP[a] (F1c+TTTT+F2) | 1121-1100 1050-1069 | (F1c) (F2) | TTGGCCGCCTCCATATTCATCATTTTCA GCTGCGTGACTATCATGT | 4 |
| WNV BIP[a] (B1c+TTTT+B2) | 1144-1165 1208-1190 | (B1) (B2c) | TGCTATTTGGCTACCGTCAGCGTTTTT GAGCTTCTCCCATGGTCG | 17 |
| WNV LF[a] | 1093-1075 | | CATCGATGGTAGGCTTGTC | 18 |
| WNV LB[a] | 1169-1186 | | TCTCCACCAAAGCTGCGT | 19 |
| CHIKV F3[b] | 10294-10312 | | ACGCAATTGAGCGAAGCAC | 20 |
| CHIKV B3[b] | 10498-10480 | | CTGAAGACATTGGCCCCAC | 21 |
| CHIKV FIP[b] (F1c+TTTT+F2) | 10378-10357 10316-10335 | (F1c) (F2) | CGGATGCGGTATGAGCCCTGTATTTTT GGAGAAGTCCGAATCATGC | 22 |
| CHIKV BIP[b] (B1+TTTT+B2c) | 10391-10413 10472-10453 | (B1) (B2c) | TCCGCGTCCTTTACCAAGGAAATTTTT TTGGCGTCCTTAACTGTGAC | 23 |
| CHIKV LF[b] | 10355-10339 | | GCTGATGCAAATTCTGT | 24 |
| CHIKV LB[b] | 10430-10446 | | CCTATGCAAACGGCGAC | 25 |

[a] Sequences from Panda M et al., "Real-time reverse transcription loop-mediated isothermal amplification for rapid detection of West Nile virus," J. Clin. Microbiol. 2004 Jan; 42(1):257-63.
[b] Sequences from Panda MM et al., "Rapid and real-time detection of Chikungunya virus by reverse transcription loop-mediated isothermal amplification assay," J. Clin. Microbiol. 2007 Feb; 45(2):351-7.
[c] Genome positions are based on MS2 (GenBank accession no. NC_001417.2), WNV strain NY99 (GenBank accession no. AF196835), and CHIKV African prototype strain S27 (GenBank accession no. AF369024).

Sequence for inner primers FIP and BIP is shown separating out the F1c, F1, B1c, or B1 region (underlined) followed by the F2, F2c, B2, or B2c region (not underlined). The complete FIP primer sequence is obtained by concatenating the F1c and F2 sequences (FIP=F1c+F2), and likewise for BIP. Primers designed by Parida et al. (see Parida M et al., "Real-time reverse transcription loop-mediated isothermal amplification for rapid detection of West Nile virus," J. Clin. Microbiol. 2004 January; 42(1):257-63; and Parida M M et al., "Rapid and real-time detection of Chikungunya virus by reverse transcription loop-mediated isothermal amplification assay," J. Clin. Microbiol. 2007 February; 45(2):351-7) also included a TTTT linker between the two segments of the inner primers.

Fluorescently-labeled primers used for QUASR endpoint detection are denoted with associated fluorophore tags and complementary quencher probe sequences in Table 2. The present invention encompasses a quench probe including a nucleic acid sequence that is substantially identical (e.g., has at least about 90% sequence identity) to any one of SEQ ID NOs:2-8 and 26-32 (absent the 3'-label) and having an optional label (e.g., a quencher label at the 3'- or 5'-terminus).

TABLE 2

QUASR primers and quench probes

| Primer Name-Fluor | Quench Probe Name | Quench Probe Sequence | SEQ ID NO: |
|---|---|---|---|
| MS2 FTP-Cy5 | MS2 FIPc-12 | AGACGATACGAT-IBRQ | 2 |
| MS2 FIP-FAM | MS2 FIPc-13 | GAGACGATACGAT-IBFQ | 3 |
| WNV FIP-ROX | WNV FIPc-25 | AAATGATGAATATGGAGG CGGCCAA-IBRQ | 5 |
| | WNV FIPc-25m | AAATGATGAATATGGAGG CAGCCAA-IBRQ | 6 |
| | WNV FIPc-15 | TATGGAGGCGGCCAA-IBRQ | 26 |
| | WNV FIPc-12 | GGAGGCGGCCAA-IBRQ | 27 |
| | WNV FIPc-10 | AGGCGGCCAA-IBRQ | 7 |
| | WNV FIPc-10m | AGGCCGCCAA-IBRQ | 8 |
| | WNV FIPc-9 | TGGCGGCCAA-IBRQ | 28 |
| | WNV FIPc-8 | TAGCGGCCAA-IBRQ | 29 |
| | WNV FIPc-7 | TAACGGCCAA-IBRQ | 30 |

TABLE 2 -continued

QUASR primers and quench probes

| Primer Name-Fluor | Quench Probe Name | Quench Probe Sequence | SEQ ID NO: |
|---|---|---|---|
| WNV LB-Cy3 | WNV LBc-12 | CTTTGGTGGAGA-IBFQ | 31 |
| CHIKV BIP-FAM | CHIKV BIPc-11 | AAGGACGCGGA-IBFQ | 32 |

Fluorophores were attached to primers at 5' end.
Quenchers were attached to quench probes at the 3' end.
IBFQ, IBRQ = Iowa Black FQ and Iowa Black RQ (dark quenchers available from Integrated DNA Technologies, Coralville, IA).

In Table 2, quench probes in bold were found to be non-inhibitory to LAMP. Underlined bases in quench probe sequence indicate non-hybridizing or mismatched bases, which are included to reduce the T. of the quencher-primer duplex. For quenchers with complementary sequences less than 10 bases (e.g. WNV FIPc-7, -8, and -9), mismatched bases were included at the 5'-end of the quencher to achieve a total length of 10 bases, which is the minimum required by the manufacturer for small-scale synthesis and HPLC purification.

Viral Culture and RNA Extraction Methods

Viral isolates noted in the text (WNV isolate L-CA-04 SAC-04-7168, GenBank accession no. DQ080059 and CHIKV strain Ross, GenBank accession no. AF490259) were pulled from a library of isolates archived at −80° C. From each isolate, RNA was extracted and plaque assays were performed to obtain viral titers. RNA was extracted using a MagMax™ magnetic particle processor (Life Technologies, Grand Island, N.Y., USA), MagMAX™-96 Viral RNA Isolation Kit (Life Technologies, Grand Island, N.Y., USA), and manufacturer provided protocols.

Plaque assays were performed using Vero cell cultures grown to confluence in six well plates, cultured with Dulbecco's Modified Eagle Medium (DMEM) supplemented with 10% fetal bovine serum (FBS) and 500 U/mL penicillin and 0.5 mg/mL streptomycin, and maintained at 37° C. and 5% $CO_2$. Virus isolates were diluted in a 10-fold serial dilution, media was removed from each well of the 6-well plate and 200 µL of diluted virus was allowed to incubate on the monolayer for 60 minutes at 37° C. A double overlay system was used where the first overlay contained nutritive media and 5% agarose. The second overlay was applied and additionally contained 0.005% neutral red, the optimal days to count plaque occurred 1-3 days after the second overlay. WNV and CHIKV viral culture should be performed at biosafety level three (BSL-3) containment. RNA from positive-sense RNA viruses (including WNV and CHIKV) is potentially infectious and should be handled carefully.

Characterization of RT-LAMP Primer Set for MS2 Phage

Here, we report a novel primer set for detection of MS2 phage by RT-LAMP. LAMP primer sequences are given in Table 1. We have characterized the primer set's sensitivity and speed using an MS2 phage RNA standard (United States Biological #R2033-18; approximately $2.51 \times 10^{11}$ copies/µL) and intact MS2 phage particles (ATCC #15597-B1). To prepare a standard curve, RT-LAMP with real-time monitoring was performed as described in Example 3, using 2 µM SYTO® 82 for detection, with the exception that monitoring was performed in an MJ Opticon 2 real-time thermocycler, as opposed to the Bio-Rad CFX instruments used otherwise. A serial 10-fold dilution of the MS2 RNA standard was used as the template.

A standard curve was generated for the MS2 RNA standard by qRT-PCR, using the MS2 primer and probe set described by Ninove L et al., "RNA and DNA bacteriophages as molecular diagnosis controls in clinical virology: a comprehensive study of more than 45,000 routine PCR tests," PLoS One 2011 Feb. 9; 6(2):e16142 (7 pp.):

TABLE 3

MS2 primers and probe used for qRT-PCR

Figure 17:
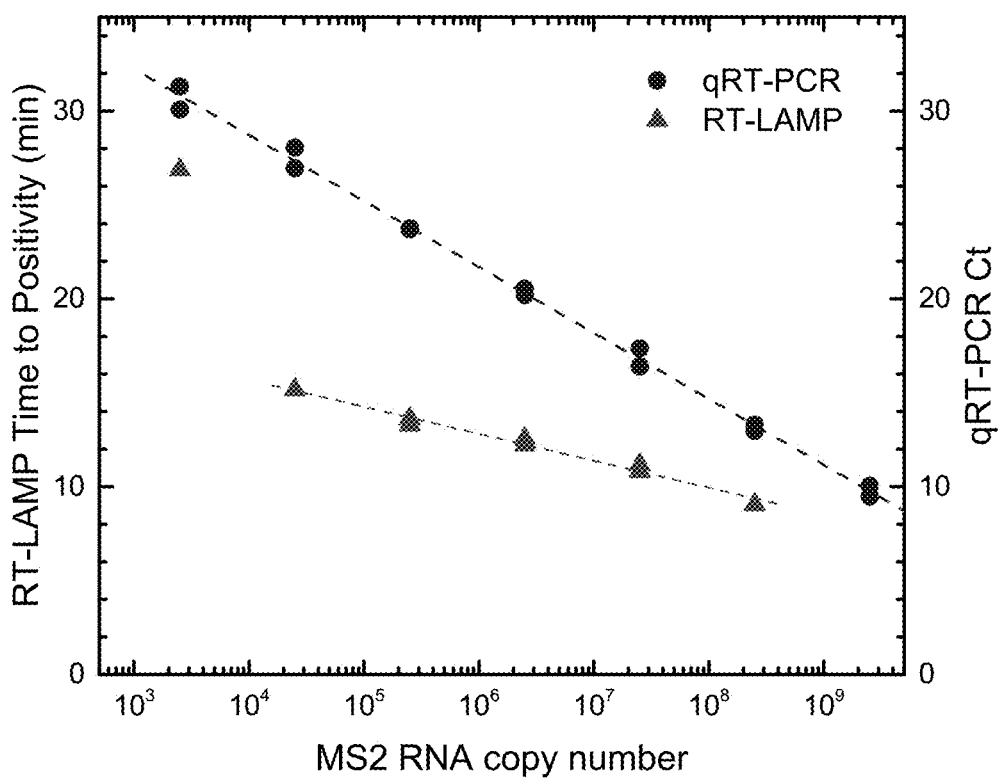
FIG. 17 shows a standard curve for MS2 RNA detection by RT-LAMP and qRT-PCR.

| MS2 Primer/probe | Sequence | SEQ ID NO: |
|---|---|---|
| Forward | CTCTGAGAGCGGCTCTATTGGT | 33 |
| Reverse | GTTCCCTACAACGAGCCTAAATTC | 34 |
| Probe | FAM-TCAGACACGCGGTCCGCTATAACGA-Iowa Black FQ | 35 | qRT-PCR reactions were performed using a one-step RT-PCR kit (iTaq Universal Probes One-Step Kit, BioRad, Hercules, Calif.) and Bio-Rad CFX96 instrument, with detection in the FAM channel. Forward and reverse primers were used at 500 nM each, and probes at 200 nM, in a total reaction volume of 10 µL. PCR was performed with an initial reverse transcription step at 50° C. for 10 minutes, followed by an initial denaturation for 50 seconds, then 40 cycles of 95° C. for 15 seconds and 60° C. for 30 seconds followed by a plate read. The qRT-PCR standard curve (Ct versus RNA copy number) is plotted on the same axes as the RT-LAMP standard curve (Time to positivity versus RNA copy number) in FIG. 17. qRT-PCR failed to detect the MS2 RNA at the next lowest dilution (approximately 250 template copies/10 µL reaction). At approximately 2500 template copies, the RT-LAMP assay showed amplification in only 1 of 2 replicates, suggesting that this is below the limit of reliable detection. We note that the linear range of the qRT-PCR assay extends approximately one log lower in template concentration than the RT-LAMP standard curve. We have observed this phenomenon when comparing qRT-PCR to RT-LAMP with several other viral RNA templates as well, which has led us to the general observation that RT-LAMP is less reliable for quantitation than qRT-PCR at low template concentrations.

Reduction of False Positives by QUASR LAMP

Figure 18:
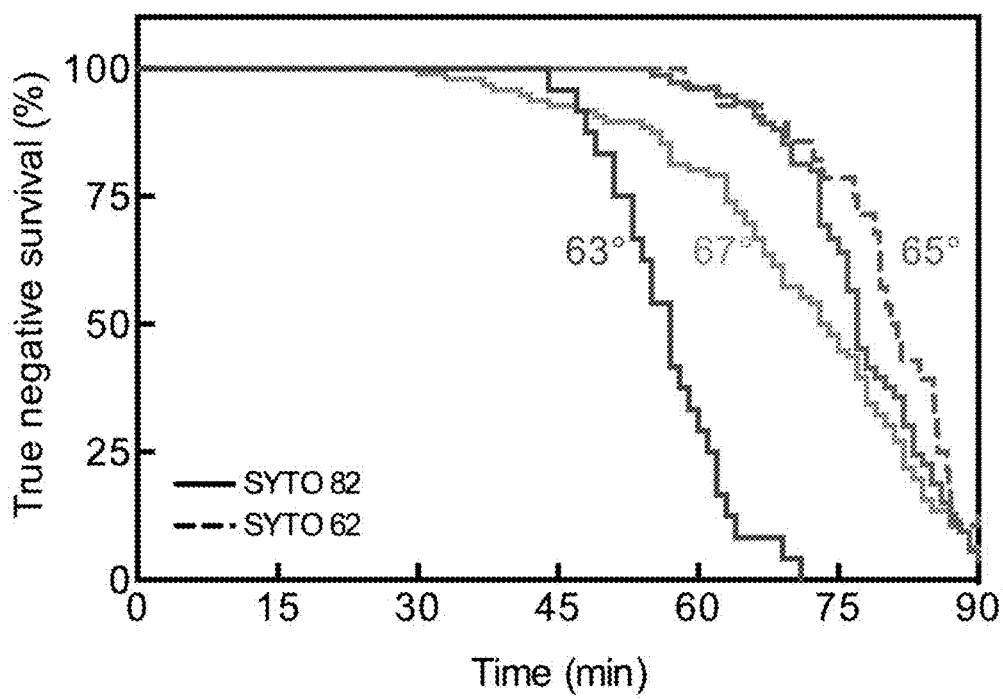
FIG. 18 shows the onset of false-positive amplification is represented by "survival" curves for true negative RT-LAMP reactions using the WNV primer set from Parida M et al., "Real-time reverse transcription loop-mediated isothermal amplification for rapid detection of West Nile virus," *J. Clin. Microbiol.* 2004 January; 42(1):257-63. Reactions carried out at 63° C. (24 observations) are more prone to false positive generation than those carried out at 67° C. (92 observations) or 65° C. (59 observations for SYTO® 82, 25 observations for SYTO® 62). There is no significant difference between the survival curves when using SYTO® 82 versus SYTO® 62.

Because LAMP utilizes six primers targeting eight regions, as opposed to two primers in the case of PCR, LAMP has a greater likelihood of primer-primer interactions leading to non-specific amplification products in the absence of a template. Consequently, detection techniques that rely on measuring nonspecific generation of double stranded DNA are prone to generate false positives. For example, the WNV primer set, originally reported by Panda M et al., "Real-time reverse transcription loop-mediated isothermal amplification for rapid detection of West Nile virus," J. Clin. Microbiol. 2004 January; 42(1):257-63, regularly gives rise to false positives in no-template controls. Usually, false positives occur after a long time (after 45 minutes), but they occasionally appear in less than 30 minutes. We have found that varying the temperature of the reaction affects the onset of false-positive amplification in no-template controls, but that changing SYTO® dyes has no effect on false positive generation (FIG. 18). The nature of false positives detected by SYTO® dyes can be attributed to primer-dimers and spurious amplification. We often observed multiple melting peaks in false positive LAMP amplicons. Furthermore, gel electrophoresis and Sanger sequencing of false positive LAMP amplicons show that they have a unique structure comprising concatamers of LAMP primers implicated in primer dimer formation and lack the unique amplified region of the WNV genome between the forward and reverse inner primers. Modifying the Parida primer set to eliminate primer-dimers resulted in reduced rates of false positive generation.

QUASR detection greatly reduces the rate of false positives due to the specificity of the quencher probe detecting incorporation of its corresponding labeled LAMP primer into an amplicon (Table 3). Theoretically, QUASR RT-LAMP can still generate false positives if the dye-labeled primer is incorporated to a high degree into the amplification product. In practice, we do see a much lower frequency of false positives with QUASR RT-LAMP compared to detection with SYTO® dyes, suggesting that the labeled primers are not being incorporated into the non-template-specific amplification products. Although the complete set of mechanisms leading to non-specific amplification are not yet known, a useful guideline is to choose a primer for labeling that has low complementarity to other primers in the set. Since false positives tend to occur at late amplification times, the combination of QUASR detection with a defined cutoff time for the reaction (e.g., 45 minutes) is expected to provide greater confidence in results. The robust resistance to false positives with QUASR detection is expected to improve the predictive value of RT-LAMP for viruses with low prevalence in the target population—for example, with surveillance for arboviruses (e.g., WNV) where the minimum infection rate of mosquitoes may be significantly less than 1% even during periods of epizootic transmission (see, e.g., Hayes E B et al., "Epidemiology and transmission dynamics of West Nile virus disease," Emerg. Infect. Dis. 2005 August; 11(8):1167-73).

TABLE 3

False positive rates for detection of WNV

| Reporter Mixture | Decision fluorophore | False Positives, X/Y (%) |
|---|---|---|
| SYTO ® only | SYTO ® 62 | 25/28 (89%) |
| SYTO ® + QUASR (all) | SYTO ® 62 | 42/117 (36%) |
|  | QUASR (all) | 0/117 (0%) |
| QUASR only (all) | QUASR (all) | 1/80 (1%)* |

*A single false positive was observed using QUASR with LB-ROX/LBc-11. All QUASR fluorescent primers/quenching probes were tested in the absence of SYTO ® 62 with 16 replicates.

Rates were determined by RT-LAMP using the primer set from Parida M et al., "Real-time reverse transcription loop-mediated isothermal amplification for rapid detection of West Nile virus," J. Clin. Microbiol. 2004 January; 42(1): 257-63. False positives are reported at 90-minute endpoints as determined by the SYTO® 62 signal or the QUASR fluorescent primer and quenching probe.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A method for detecting a presence of a target nucleic acid in a sample in a loop-mediated isothermal amplification reaction, the method comprising:
combining the sample with a first primer, a quench probe, and a polymerase to provide a reaction mixture, wherein the first primer comprises a first nucleic acid sequence having sufficient complementarity to a site in the target nucleic acid, and wherein the quench probe comprises a second nucleic acid sequence having sufficient complementarity to a first portion of the first primer and a quencher label operably linked to the second nucleic acid sequence;
amplifying the target nucleic acid sequence, if present, in the reaction mixture by incubating at a temperature $T_1$; and
promoting hybridization of the quench probe to the first primer by cooling to a temperature $T_3$, wherein $T_3$ is less than $T_1$;
detecting the presence of the target nucleic acid in the sample based on fluorescence of the sample at an endpoint of the isothermal amplification reaction;
wherein the first primer is not a loop primer; and
wherein the first nucleic acid sequence has at least 90% sequence identity to any one of SEQ ID NOs: 1 and 10-12 and optionally having a label at a 3'- or 5'-terminus; or
wherein the second nucleic acid sequence has at least 90% sequence identity to any one of SEQ ID NOs: 2-8 and 26-32 and optionally having a label at a 3'-5' terminus.

2. The method of claim 1, further comprising, after the amplifying step:
inactivating the polymerase in the reaction mixture by heating to a temperature $T_2$,
wherein $T_2$ is greater than $T_1$ and wherein $T_2$ is greater than $T_3$.

3. The method of claim 2, wherein the combining step, the amplifying step, the inactivating step, and the promoting step are conducted in a single reaction chamber.

4. The method of claim 3, wherein the reaction chamber is a microfluidic chamber.

5. The method of claim 1, wherein the first primer further comprises a fluorescent label operably linked to the first nucleic acid sequence, and wherein the quencher label and the fluorescent label are in proximity to each other when the quench probe is hybridized to the first primer.

6. The method of claim 1, wherein the quencher label comprises a molecule or a functional group that absorbs and excites emitted light of a fluorophore, but does not emit light itself.

7. The method of claim 1, wherein in the combining step, further combining a reverse transcriptase, and the reaction mixture further comprising a reverse transcriptase.

8. The method of claim 1, wherein the isothermal amplification reaction is a multiplexed loop-mediated isothermal amplification reaction and the combining step further includes a plurality of different primers and a plurality of corresponding different quench probes.

9. The method of claim 1, wherein in the combining step, further combining one or more additional reagents selected from the group consisting of a divalent cation, a buffer, a nucleotide, a deoxynucleotide, a reverse transcriptase, and an enhancing agent.

10. The method of claim 9, wherein the quench probe, the first primer, a signal probe, if present, and/or the one or more additional reagents is provided in a dried form, a freeze dried form, and/or a lyophilized form.

11. The method of claim 1 wherein the first primer is an inner primer.

12. The method of claim 1, wherein the first nucleic acid sequence has at least 90% sequence identity to any one of SEQ ID NOs: 1 and 10-12 and optionally having a label at a 3'- or 5' terminus.

13. The method of claim 1, wherein the second nucleic acid sequence has at least 90% sequence identity to any one of SEQ ID NOs: 2-8 and 26-32 and optionally, having a label at a 3'-5' terminus.

14. A method for detecting a presence of a target nucleic acid in a sample in an isothermal amplification reaction, the method comprising:
combining the sample with a first primer, a quench probe, and a polymerase to provide a reaction mixture, wherein the first primer comprises a first nucleic acid sequence having sufficient complementarity to a site in the target nucleic acid, and wherein the quench probe comprises a second nucleic acid sequence having sufficient complementarity to a first portion of the first primer and a quencher label operably linked to the second nucleic acid sequence;
amplifying the target nucleic acid sequence, if present, in the reaction mixture by incubating at a temperature $T_1$; and
promoting hybridization of the quench probe to the first primer by cooling to a temperature $T_3$, wherein $T_3$ is less than $T_1$;
detecting the presence of the target nucleic acid in the sample based on fluorescence of the sample at an endpoint of the isothermal amplification reaction;
wherein the reaction mixture further comprises a signal probe comprising a third nucleic acid sequence having sufficient complementarity to a second portion of the first primer and further comprising a fluorescent label operably linked to the third nucleic acid sequence;
wherein the first portion and the second portion are in proximity to each other in the first primer; and wherein the quench probe and the signal probe hybridize to the first primer and the quencher label and the fluorescent label are in proximity to each other when the quench probe and the signal probe are hybridized to the first primer;

wherein the first nucleic acid sequence has at least 90% sequence identity to any one of SEQ ID NOs: 1 and 10-14 and optionally having a label at a 3'- or 5'-terminus; and wherein the second nucleic acid sequence has at least 90% or greater sequence identity to any one of SEQ ID NOs: 2-8 and 26-32 and optionally having a label at a 3'-5' terminus.

15. The method of claim 14, wherein the quench probe comprises one or more base mismatches, as compared to a nucleic acid sequence that is perfectly complementary to the first portion of the first primer; and/or wherein the signal probe comprises one or more base mismatches, as compared to a nucleic acid sequence that is perfectly complementary to the second portion of the first primer.

16. The method of claim 14 wherein a concentration of the quench probe is in excess of a concentration of a signal probe.

17. The method of claim 14, wherein the first primer or an additional primer is selected from the group consisting of SEQ ID Nos.: 13, 14, 18, 19, 24, and 25.

18. A method for detecting a presence of a target nucleic acid in a sample in an isothermal amplification reaction, the method comprising:

combining the sample with a first primer, a quench probe, and a polymerase to provide a reaction mixture, wherein the first primer comprises a first nucleic acid sequence having sufficient complementarity to a site in the target nucleic acid, and wherein the quench probe comprises a second nucleic acid sequence having sufficient complementarity to a first portion of the first primer and a quencher label operably linked to the second nucleic acid sequence;

amplifying the target nucleic acid sequence, if present, in the reaction mixture by incubating at a temperature $T_1$;

promoting hybridization of the quench probe to the first primer by cooling to a temperature $T_3$, wherein $T_3$ is less than $T_1$; and detecting the presence of the target nucleic acid in the sample based on fluorescence of the sample at an endpoint of the isothermal amplification reaction;

wherein a melting temperature Tm of the quench probe is from 10° C. to 45° C.;

wherein primers are selected that do not form stable hairpin formations or self-dimerize;

wherein more than 50% up to 100% of a total primer content is fluorescent labeled primer;

wherein the first primer or an additional primer is selected from the group consisting of SEQ ID Nos.: 13, 14, 18, 19, 24, and 25.

19. The method of claim 18, wherein the Tm of the quench probe is at least 5° C. lower than a temperature of the amplification reaction with the reaction mixture.

20. The method of claim 19, wherein a length of the quench probe is six to thirteen nucleotides.

* * * * *

SEQUENCE LISTING

<160> NUMBER OF SEQ ID NOS: 37

<210> SEQ ID NO 1
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Optional probe (e.g., a signal probe)

<400> SEQUENCE: 1
atcgtatcgt ctcgccatct accaccagag ctatattcat atc          43

<210> SEQ ID NO 2
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: Optional probe (e.g., IBRQ)

<400> SEQUENCE: 2
agacgatacg at                                                      12

<210> SEQ ID NO 3
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (13)..(13)
<223> OTHER INFORMATION: Optional probe (e.g., IBFQ)

<400> SEQUENCE: 3
gagacgatac gat                                                     13

<210> SEQ ID NO 4
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Optional probe (e.g., a signal probe)

<400> SEQUENCE: 4
ttggccgcct ccatattcat cattttcagc tgcgtgacta tcatgt                 46

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (25)..(25)
<223> OTHER INFORMATION: Optional probe (e.g., IBRQ)

<400> SEQUENCE: 5
aaatgatgaa tatggaggcg gccaa                                        25

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (25)..(25)
<223> OTHER INFORMATION: Optional probe (e.g., IBRQ)

<400> SEQUENCE: 6
aaatgatgaa tatggaggca gccaa                                        25

<210> SEQ ID NO 7
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: Optional probe (e.g., IBRQ)

```
<400> SEQUENCE: 7
aggcggccaa                                                           10

<210> SEQ ID NO 8
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: Optional probe (e.g., IBRQ)

<400> SEQUENCE: 8
aggccgccaa                                                           10

<210> SEQ ID NO 9

<400> SEQUENCE: 9

000

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
cttgcgacga tagacttatc                                                20

<210> SEQ ID NO 11
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 11
tagatgccta tggttccg                                                  18

<210> SEQ ID NO 12
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 12
acaatgggaa atgggttcac agggtcgctt tgactattg                            39

<210> SEQ ID NO 13
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 13
gattccgtag tgtgagcg                                                  18

<210> SEQ ID NO 14
<211> LENGTH: 22
<212> TYPE: DNA
```

```
<213> ORGANISM: Artificial Sequence
<220> FEATURE:
<223> OTHER INFORMATION: Synthetic oligonucleotide

<400> SEQUENCE: 14
gctagagtcc atgatattct gg                                              22

<210> SEQ ID NO 15
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 15
tggatttggt tctcgaagg                                                  19

<210> SEQ ID NO 16
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 16
ggtcagcacg tttgtcatt                                                  19

<210> SEQ ID NO 17
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 17
tgctatttgg ctaccgtcag cgttttttgag cttctcccat ggtcg                    45

<210> SEQ ID NO 18
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 18
catcgatggt aggcttgtc                                                  19

<210> SEQ ID NO 19
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 19
tctccaccaa agctgcgt                                                   18

<210> SEQ ID NO 20
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 20
acgcaattga gcgaagcac                                                  19
```

<210> SEQ ID NO 21
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 21
ctgaagacat tggccccac                                                    19

<210> SEQ ID NO 22
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 22
cggatgcggt atgagccctg tattttttgga gaagtccgaa tcatgc                     46

<210> SEQ ID NO 23
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 23
tccgcgtcct ttaccaagga aatttttttg gcgtccttaa ctgtgac                    47

<210> SEQ ID NO 24
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 24
gctgatgcaa attctgt                                                      17

<210> SEQ ID NO 25
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 25
cctatgcaaa cggcgac                                                      17

<210> SEQ ID NO 26
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (15)..(15)
<223> OTHER INFORMATION: Optional probe (e.g., IBRQ)

<400> SEQUENCE: 26
tatggaggcg gccaa                                                        15

<210> SEQ ID NO 27

```
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: Optional probe (e.g., IBRQ)

<400> SEQUENCE: 27
ggaggcggcc aa                                                     12

<210> SEQ ID NO 28
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: Optional probe (e.g., IBRQ)

<400> SEQUENCE: 28
tggcggccaa                                                        10

<210> SEQ ID NO 29
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: Optional probe (e.g., IBRQ)

<400> SEQUENCE: 29
tagcggccaa                                                        10

<210> SEQ ID NO 30
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: Optional probe (e.g., IBRQ)

<400> SEQUENCE: 30
taacggccaa                                                        10

<210> SEQ ID NO 31
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: Optional probe (e.g., IBFQ)

<400> SEQUENCE: 31
ctttggtgga ga                                                     12
```

```
<210> SEQ ID NO 32
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: Optional probe (e.g., IBFQ)

<400> SEQUENCE: 32
aaggacgcgg a                                                          11

<210> SEQ ID NO 33
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 33
ctctgagagc ggctctattg gt                                              22

<210> SEQ ID NO 34
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 34
gttccctaca acgagcctaa attc                                            24

<210> SEQ ID NO 35
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Optional probe (e.g., FAM)
<220> FEATURE:
<221> NAME/KEY: misc_feature
<222> LOCATION: (25)..(25)
<223> OTHER INFORMATION: Optional probe (e.g., IBFQ)

<400> SEQUENCE: 35
tcagacacgc ggtccgctat aacga                                           25

<210> SEQ ID NO 36
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: Optional probe (e.g., Cy3)

<400> SEQUENCE: 36
gattccgtag tgtgagcg                                                   18

<210> SEQ ID NO 37
<211> LENGTH: 13
<212> TYPE: DNA
```

```
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (13)..(13)
<223> OTHER INFORMATION: Optional probe (e.g., IBFQ)

<400> SEQUENCE: 37
acactacgga atc                                                          13
```